United States Patent [19]
Markham et al.

[11] Patent Number: 5,952,481
[45] Date of Patent: Sep. 14, 1999

[54] DNA ENCODING UBIQUITIN CONJUGATING ENZYMES

[75] Inventors: Alexander Fred Markham, Goostrey; Philip Alan Robinson, Bradford, both of United Kingdom

[73] Assignee: The University of Leeds, United Kingdom

[21] Appl. No.: 08/718,538

[22] PCT Filed: Mar. 29, 1995

[86] PCT No.: PCT/GB95/00707

§ 371 Date: Nov. 13, 1996

§ 102(e) Date: Nov. 13, 1996

[87] PCT Pub. No.: WO95/27066

PCT Pub. Date: Oct. 12, 1995

[30] Foreign Application Priority Data

Mar. 31, 1994 [GB] United Kingdom .................... 9406577
Mar. 31, 1994 [GB] United Kingdom .................... 9411978
Mar. 31, 1994 [GB] United Kingdom .................... 9423702

[51] Int. Cl.$^6$ ............................. C07H 21/04; C12N 15/00
[52] U.S. Cl. ...................... 536/23.2; 536/24.3; 435/320.1
[58] Field of Search ........................... 435/6, 91.2, 320.1, 435/240.2, 252.3, 254.2, 172.3, 69.1; 536/23.2, 24.3, 24.33, 26.6; 530/350

[56] References Cited

U.S. PATENT DOCUMENTS 5,384,255  1/1995  Ciechanover et al. ................... 435/193

OTHER PUBLICATIONS

Structural and Functional Conservation of Two Human Homologs of Yeast DNA Repair Gene RAD6, Proc. Natl. Acad. Sci. USA, (Biochemistry), vol. 88, pp. 8865–8869 (1991), M.Koken et al.

cDNA Cloning of Novel Human Ubiquitin Carrier Protein, The Journal of Biological Chemistry, vol. 267, No. 22 pp. 15829–15835 (1992), Z. Liu et al.

Cloning of the Human Homolog of the CDC34 Cell Cycle Gene by Complementation in Yeast, Proc. Natl. Acad. Sci USA (Genetics), vol. 90, pp. 10484–10488 (1993), S. E. Plon et al.

A Human Ubiquitin–Conjugating Enzyme Homologous to Yeast UBC8, The Journal of Biological Chemistry, vol. 269, No. 12, pp. 8797–8802, (Mar., 1994), P. Kaiser et al.

Homologs of the Essential Ubiquitin Conjugating Enzymes UBC1, 4 and 5 in Yeast are Encoded by a Multigene Family in Arabidopsis Thaliana, The Plant Journal, 3(4), pp. 545–552, (1993), Girod et al.

Purification and Characterization of a Novel Species of Ubiquitin–Carrier Protein, E2, That Is Involved in Degradation of Non–"N–end Rule" Protein Substrates, The Journal of Biological Chemistry, vol. 269, pp. 9574–9581, (Apr. 1994), N. Blumenfeld et al.

Cloning of a Gene Bearing Missense Mutations in Early–Onset Familial Alzheimer's Disease, Nature, vol. 375, pp. 754–760 (Jun. 1995) R. Sherrington et al.

Identification of a Human Ubiquitin–Conjugating Enzyme that Mediates the E6–Ap–dependent Ubiquitination of p53, Proc. Natl. Acad. Sci USA (Biochemistry), vol. 91, pp. 8797–8801, (Sep. 1994) M. Scheffner et al.

Degradation of the Tumor Suppressor Protein p53 by the Ubiquitin–Medicated Proteolytic System Requires a Novel Species of Ubiquitin–Carrier Protein, E2, Journal of Biological Chemistry, vol. 269, pp. 9582–9589, (Apr. 1994), A. Ciechanover et al.

*Primary Examiner*—Eggerton A. Campbell
*Attorney, Agent, or Firm*—Fulbright & Jaworski, LLP

[57] ABSTRACT

The invention relates to methods for determining a predisposition for and diagnosing the existence of a degenerative disease or a cancer and also products and processes for treating and obtaining treatments for such a degenerative disease or a cancer. The invention has particular application in the use of information concerning the elucidation of DNA and amino acid sequence structure relating to human and mouse ubiquitin conjugating enzymes.

17 Claims, 21 Drawing Sheets

FIG. 1

| | |
|---|---:|
| ccagcctcgccaatatggtgaaacccgtttctactaaaaatatttaaaaaattagccagg | 60 |
| cgtggtggcaatcacctgtaatctcagttactcgggaggctgagacaggagaattgcttg | 120 |
| aactcaagaggcagaggttgcagtgagccaagattgagccactacaccccagcctgggta | 180 |
| acacagggagactccatctcaaaaataaaataaaataaaataaacaggaggaaggagcag | 240 |
| caccaaatccaagatggcggccagcaggaggctgatgaaggagcttgaagaaatccgcaa | 300 |

M  A  A  S  R  R  L  M  K  E  L  E  E  I  R  K
          1                                10

| | |
|---|---:|
| atgtgggatgaaaaacttctgtaacatccaggttgatgaagctaatttattgacttggca | 360 |

C  G  M  K  N  F  C  N  I  Q  V  D  E  A  N  L  L  T  W  Q
      20                           30

| | |
|---|---:|
| agggcttattgttcctgacaaccctccatatgataaggggggccttcagaatagaaatcaa | 420 |

G  L  I  V  P  D  N  P  P  Y  D  K  G  A  F  R  I  E  I  N
    40                      50

| | |
|---|---:|
| ctttccagcagagtacccattcaaaccaccgaagatcacatttaaaacaaagatctatca | 480 |

F  P  A  E  Y  P  F  K  P  P  K  I  T  F  K  T  K  I  Y  H
      60                        70

| | |
|---|---:|
| cccaaacatcgacgaaaaggggcaggtctgtctgccagtaattagtgctgaaaactggaa | 540 |

P  N  I  D  E  K  G  Q  V  C  L  P  V  I  S  A  E  N  W  K
      80                        90

| | |
|---|---:|
| gccagcaaccaaaaccgaccaagtaatccagtccctcatagcactggtgaatgacccca | 600 |

P  A  T  K  T  D  Q  V  I  Q  S  L  I  A  L  V  N  D  P  Q
      100                     110

| | |
|---|---:|
| gcccaagcacccgcttcgggctgacctagctgaagaatactctaaggaccgtaaaaaatt | 660 |

P  K  H  P  L  R  A  D  L  A  E  E  Y  S  K  D  R  K  K  F
      120                     130

| | |
|---|---:|
| ctgtaagaatgctgaagagtttacaaagaaatatggggaaaagcgacctgtggactaaaa | 720 |

C  K  N  A  E  E  F  T  K  K  Y  G  E  K  R  P  V  D  *
      140                     150

| | |
|---|---:|
| tctgccacgattggttccagcaagtgtgagcagagaccccgtgcagtgcattcagacacc | 780 |
| ccgcaaagcaggactctgtggaaattgacacgtgccaccgcctggcgttcgcttgtggca | 840 |
| gttactaactttctacagttttcttaatcaaaagtggtctaggtaacctgtaaagaaagg | 900 |
| attaaaaatttaagatgttctagttctgctctctttgttttaaaaatcactgcttcaatc | 960 |
| tacttcaaaagaaaaaaaaaacaataaaaagtgttgatga | 1000 |

FIG. 2A

```
agcaccaaatccaagatggcggccagcaggaggctgatgaaggagcttgaagaaatccgc    60
                M  A  A  S  R  R  L  M  K  E  L  E  E  I  R aaatgtgggatgaaaaacttccgtaacatccaggttgatgaagctaatttattgacttgg   120
 K  C  G  M  K  N  F  R  N  I  Q  V  D  E  A  N  L  L  T  W caagggcttattgttcctgacaaccctccatatgataagggagccttcagaatcgaaatc   180
 Q  G  L  I  V  P  D  N  P  P  Y  D  K  G  A  F  R  I  E  I aactttccagcagagtacccattcaaaccaccgaagatcacatttaaaacaaagatctat   240
 N  F  P  A  E  Y  P  F  K  P  P  K  I  T  F  K  T  K  I  Y cacccaaacatcgacgaaaaggggcaggtctgtctgccagtaattagtgccgaaaactgg   300
 H  P  N  I  D  E  K  G  Q  V  C  L  P  V  I  S  A  E  N  W aagccagcaaccaaaaccgaccaagtaatccagtccctcatagcactggtgaatgacccc   360
 K  P  A  T  K  T  D  Q  V  I  Q  S  L  I  A  L  V  N  D  P cagcctgagcacccgcttcgggctgacctagctgaagaatactctaaggaccgtaaaaaa   420
 Q  P  E  H  P  L  R  A  D  L  A  E  E  Y  S  K  D  R  K  K ttctgtaagaatgctgaagagtttacaaagaaatatggggaaaagcgacctgtggactaa   480
 F  C  K  N  A  E  E  F  T  K  K  Y  G  E  K  R  P  V  D  * aatctgccacgattggttccagcaagtgtgagcagagaccccgtgcagtgcattcagaca   540 ccccgcaaagcaggactctgtggaaattgacacgtgccaccgcctggcgttcgcttgtgg   600 cagttactaactttctacagttttcttaatcaaaagtggtctaggtaacctgtaaagaaa   660 ggattaaaaatttaagatgttct                                       683
```

FIG. 2B

```
cagaatttggataaataggaggcagctttggcttaaaagcacattagctgtaaatcagtt gtaaagccagagttttgttcccggattagctgcctcttgcctgtgccatttctgagactg tgttaacccccatgccttgtccttctcttggcagTAATCCAGTCCCTCATAGCACTGGT     350
                                  I  Q  S  L  I  A  L  V GAATGACCCCCAGCCTGAGCACCCGCTTCGGGCTGACCTAGCTGAAGAATACTCTAAGGA    410
 N  D  P  Q  P  E  H  P  L  R  A  D  L  A  E  E  Y  S  K  D CCGTAAAAAATTCTGTAAGAATGCTGAAGAGTTTACAAAGAAATATGGGGAAAAGCGACC    470
 R  K  K  F  C  K  N  A  E  E  F  T  K  K  Y  G  E  K  R  P

TGTGGACTAAAATCTGCCACGATTGGTTCCAGCAAGTGTGAGCAGAGACCCCGTGCAGTG    530
 V  D  *

CATTCAGACACCCCGCAAAGCAGGACTCTGTGGAAATTGACACGTGCCACCGCCTGGCGT    590

TCGCTTGTGGCAGTTACTAACTTTCTACAGTTTTCTTAATCAAAAGTGGTCTAGGTAACC    650

TGTAAAGAAAGGATTAAAAATTTAAGATGTTCTAGTTCTGCTCTCTTTGTTTTAAAAATG    710

ACTGCTTCAATCTACTTCAAAAGAATGGTGTTTCTTTTCTTGTCCAATTTTATCCAAAAT    770

CTTCAAGTTACATTTAACCCATAAGGTTTAAAAAAAAGGAAAAAAAACGGTTGTGGTTC    829
```

FIG. 3

```
AACTGGAAGC CAGCCACCAA GACTGTCCAA GTAATCCAGT CCCTCATAGC  50
ACTGGTGAAT GACCCCCAGC CTGAGCACCC ACTCCGGGCT GACCTAGCTG 100
AAGAATACTC TAAGGACCGT AAAAAATTCT GTAAGAATGC TGAAGAGTTT 150
ACAAAGAAAT ATGGGGAAAA GCGACCTGTG GACTAAAATC TGCCACGATT 200
GGTTCCAGCA AGTGTGAGCA GAGACCCCGA GCAGTGCATT CAGACACCCC 250
GCAAAGCAGG ACTCTGTGGA AATTGACACG TGCCACCAAC TGGCGTCCGC 300
TTGTGGCAGT TACTAACTTT CTACAGTTTT CTTAATCAAA AGTGGTCTAG 350
GTAACCTGTA A                                         361
```

FIG. 4

```
NWKPATKTVQ VIQSLIALVN DPQPEHPLRA DLAEEYSKDR KKFCKNAEEF 50
TKKYGEKRPV D                                         61
```

FIG. 10

```
HUBC4b   MAASRRLMKE  LEEIRKCGMK  NFRNIQVDEA  NLLTWQGLIV  PDNPPYDKGA
UbcH2    *SSPSPGKRR  MDTDVVKLIE  SKHEVTILGG  -*NEFVVFFYG*QGT**EG*V
UbcH5    **L-K*IQ**  *SDLQRDPPA  HCSAGP*GDD  -*FH**AT*MG*PDSA*QG*V
UBC4     *SS*K*IA**  *SDLERDPPT  SCSAGP*GDD  -*YH**AS*MG*ADS**AG*V
UbcD1    **LK*INK**  *QDLGRDPPA  QCSAGP*GDD  -*FH**AT*MG*PDS**QG*V
BEN      *SSLP*RILK  ETQRLMQEPV  PGI*AIP**N  *ARYFNVIVTG*NDS*FEG*V
Ubc-2    **LK*IQ-**  *QDLGREPPA  QCSAGP*GDD  -*FH**AT*MG*PES**QG*V

HUBC4b   FRIEINFPAE  YPFKPPKITF  KTKIYHPNID  EKGQVCLPVI  SAENWKPATK
UbcH2    QKVRVDL*DK  ****S*S*G*  MNF***EAS*T*D  -NQT*TALYD
UbcH5    *FLTVH**TD  ********A*  T********N  SN*SI**DIL  -RSQ*S**LT
UBC4     *FLS*H**TD  ********S*  T********N  AN*NI**DIL  -KDQ*S***T
UbcD1    *FLT*H**TD  *******VA*  T*R******N  SN*SI**DIL  -KSQ*S***T
BEN      *KL*LFL*ED  MSAVR*  I*********  RL*RI**D*L  -KDK*S**LQ
Ubc-2    *FLT*H**TD  *******VA*  T*R******N  SN*SI**DIL  -RSQ*S**LT

HUBC4b   TDQVIQSLIA  LVNDPQPEHP  LRADLAEEYS  KDRKKFCKNA  EEFTKKYGEK
UbcH2    LTNIFE*FLPQ*LAY*N*ID*  *NG*A*AM*L  HRPEEYKQKI  K*YIQ**ATE
UbcH5    VSK*LL*ICS  *LC**N*DD*  *VP*I*QI*K  S*KE*YNRH*  R*W*Q**AM
UBC4     LSK*LL*ICS  *LT*AN*DD*  *VPEI*HI*K  T*KA*YEAT*  R*W****AV
UbcD1    ISK*LL*ICS  *LC**N*DD*  *VPEI*RI*K  T**E*YNEL*  R*W*R**AM
BEN      IRTILL*IQ*  *LSA*N*DD*  *AN*VLWK  VNEAEAIR  R*W*Q**AVE
Ubc-2    ISK*LL*ICS  *LCD*N*DD*  *VPEI*AI*K  T**ERYNQL*  R*W*Q**AM

HUBC4b   RPVD
UbcH2    EALKEQEEGT  GDSSSESSMS  DFSEDEAQDM  EL
UbcH5
UBC4
UbcD1
BEN      D
Ubc-2
```

FIG. 11

```
            1                                                          50
HUBC4a      MAASRRLMKE LEEIRKCGMK NFCNIQVDEA NLLTWQGLIV PDNPPYDKGA
HUBC4b      ******** ****** R***** ****** ********
HUBC4c      .......... .*CN R*F***G* ******** **-*
HUBC4d      .......... .......... .......... .......... ..........
HUBC4e      .......... .......... .......... .......... ..........
MUBC4       .......... .......... .......... .......... ..........

51                                                         100
HUBC4a      FRIEINFPAE YPFKPPKITF KTKIYHPNID EKGQVCLPVI SAENWKPATK
HUBC4b      ********** ********** ********** ********** **********
HUBC4c      ********** H******S*L *DLSPKCPLK GAGLSASKLV LKTGSQQPKL
HUBC4d      .......... .......... .......... .......... ..........
HUBC4e      .......... .......... .......... .......... ..........
MUBC4       .......... .......... .......... .......... ...*******

101                                                        150
HUBC4a      TDQVIQSLIA LVNDPQPKHP LRADLAEEYS KDRKKFCKNA EEFTKKYGEK
HUBC4b      ********** *******E** ********** ********** **********
HUBC4c      TK
HUBC4d      ..******** *******E** ********** ********** *********S
HUBC4e      ..******** *******E** ********** N********* **********
MUBC4       *V******** *******E** ********** ********** **********

151
HUBC4a      RPVD
HUBC4b      ****
HUBC4c
HUBC4d      DLWTKICHDW FQQV
HUBC4e      ****
MUBC4       ****
```

FIG. 12A

```
         1                                                              50
HUBC4a   ccagcctcgc caatatggtg aaacccgttt ctactaaaaa tatttaaaaa
HUBC4b   .......... .......... .......... .......... ..........
HUBC4c   .......... .......... .......... .......... ..........
HUBC4d   .......... .......... .......... .......... ..........
HUBC4e   .......... .......... .......... .......... ..........
MUBC4    .......... .......... .......... .......... ..........

51                                                             100
HUBC4a   attagccagg cgtggtggca atcacctgta atctcagtta ctcgggaggc
HUBC4b   .......... .......... .......... .......... ..........
HUBC4c   .......... .......... .......... .......... ..........
HUBC4d   .......... .......... .......... .......... ..........
HUBC4e   .......... .......... .......... .......... ..........
MUBC4    .......... .......... .......... .......... ..........

101                                                            150
HUBC4a   tgagacagga gaattgcttg aactcaagag gcagaggttg cagtgagcca
HUBC4b   .......... .......... .......... .......... ..........
HUBC4c   .......... .......... .......... .......... ..........
HUBC4d   .......... .......... .......... .......... ..........
HUBC4e   .......... .......... .......... .......... ..........
MUBC4    .......... .......... .......... .......... ..........

151                                                            200
HUBC4a   agattgagcc actcacaccc agcctgggta acacagggag actccatctc
HUBC4b   .......... .......... .......... .......... ..........
HUBC4c   .......... .......... .......... .......... ..........
HUBC4d   .......... .......... .......... .......... ..........
HUBC4e   .......... .......... .......... .......... ..........
MUBC4    .......... .......... .......... .......... ..........

201                                                            250
HUBC4a   aaaaataaaa taaaataaaa taaacaggag gaaggagcag caccaaatcc
HUBC4b   .......... .......... .......... ........** **********
HUBC4c   .......... .......... .......... .......... ..........
HUBC4d   .......... .......... .......... .......... ..........
HUBC4e   .......... .......... .......... .......... ..........
MUBC4    .......... .......... .......... .......... ..........

251                                                            300
HUBC4a   aagatggcgg ccagcaggag gctgatgaag gagcttgaag aaatccgcaa
HUBC4b   ********** ********** ********** **********  **********
HUBC4c   .......... .......... .......... .......**** ****at****
HUBC4d   .......... .......... .......... .......... ..........
HUBC4e   .......... .......... .......... .......... ..........
MUBC4    .......... .......... .......... .......... ..........
```

FIG. 12B

```
         301                                                           350
HUBC4a   atgtgggatg aaaaacttct gtaacatcca ggttgatgaa gctaatttat
HUBC4b   ********** ********c  ********** ********** **********
HUBC4c   t***a* ******c  *t *a****g* **********
HUBC4d   .......... .......... .......... .......... ..........
HUBC4e   .......... .......... .......... .......... ..........
MUBC4    .......... .......... .......... .......... ..........

351                                                           400
HUBC4a   tgacttggca agggcttatt gttcctgaca accctccata tgataagggg
HUBC4b   ********** ********** ********** ********** ********a
HUBC4c   ********** ********** ********** ********-  --********
HUBC4d   .......... .......... .......... .......... ..........
HUBC4e   .......... .......... .......... .......... ..........
MUBC4    .......... .......... .......... .......... ..........

401                                                           450
HUBC4a   gccttcagaa tagaaatcaa ctttccagca gagtacccat tcaaaccacc
HUBC4b   ********** *c******** ********** ********** **********
HUBC4c   ********** *c****** ****** *c**** ********
HUBC4d   .......... .......... .......... .......... ..........
HUBC4e   .......... .......... .......... .......... ..........
MUBC4    .......... .......... .......... .......... ..........

451                                                           500
HUBC4a   gaagatcaca tttaaaacaa agatctatca cccaaacatc gacgaaaagg
HUBC4b   ********** ********** ********** ********** **********
HUBC4c   ***g c----- **g* ****tg ct****
HUBC4d   .......... .......... .......... .......... ..........
HUBC4e   .......... .......... .......... .......... ..........
MUBC4    .......... .......... .......... .......... ..........

501                                                           549
HUBC4a   ggcaggtctg tctgccagt- aattagtgct gaaaactgga agccagcaac
HUBC4b   ********** ********-  ********c  ********** **********
HUBC4c   ********c  ********a  ********** ********** **********
HUBC4d   .......... .......... .......... .......... ..........
HUBC4e   .......... .......... .......... .......... ..........
MUBC4    .......... .......... .......... ......**** *******c**

550                                                           599
HUBC4a   caaaaccgac caagtaatcc agtccctcat agcactggtg aatgaccccc
HUBC4b   ********** ********** ********** ********** **********
HUBC4c   ******t*** ********** ********** ********** **********
HUBC4d   .........* ********** ********** ********** **********
HUBC4e   .........* ********** ********** ********** *******g*
MUBC4    ***g**t*t* ********** ********** ********** **********
```

FIG. 12C

```
              600                                                              649
HUBC4a   agcccaagca cccgcttcgg gctgacctag ctgaagaata ctctaaggac
HUBC4b   ****tg**** ********** ********** ********** **********
HUBC4c   **tg*c ta**a* ******** *t ********
HUBC4d   *****g**** ********** ********** ********** **********
HUBC4e   *****g**** ********** ********** ********** ******c***
MUBC4    **tg *ac* ******** ****** ********

650                                                              699
HUBC4a   cgtaaaaaat tctgtaagaa tgctgaagag tttacaaaga aatatgggga
HUBC4b   ********** ********** ********** ********** **********
HUBC4c   t*****t*t* ********** ******__** ******g*** ****g*****
HUBC4d   ********** ********** ********** ********** ********_
HUBC4e   ********** ********** ********** ********** **********
MUBC4    ********** ********** ********** ********** **********

700                                                              749
HUBC4a   aaagcgacct gtggactaaa atctgccacg attggttcca gcaagtgtga
HUBC4b   ********** ********** ********** ********** **********
HUBC4c   ********t* a*** *****a *c** *t********
HUBC4d   ****t***** ********** ********** ********** *******a*
HUBC4e   ******** ****** g***** ****** ********
MUBC4    ******** ****** ******t* *ga* **t*

750                                                              799
HUBC4a   gcagagaccc cgtgcagtgc attcagacac cccgcaaagc aggactctgt
HUBC4b   ********** ********** ********** ********** **********
HUBC4c   **********  ..........  ..........  ..........  ..........
HUBC4d   ******g*** *a........  ..........  ..........  ..........
HUBC4e   ********** **........  ..........  ..........  ..........
MUBC4    ******** a***** ****** ****** ********

800                                                              849
HUBC4a   ggaaattgac acgtgccacc gcctggcgtt cgcttgtggc agttactaac
HUBC4b   ********** ********** ********** ********** **********
HUBC4c   ..........  ..........  ..........  ..........  ..........
HUBC4d   ..........  ..........  ..........  ..........  ..........
HUBC4e   ..........  ..........  ..........  ..........  ..........
MUBC4    ********** ********** aa******c* ********** **********

850                                                              899
HUBC4a   tttctacagt tttcttaatc aaaagtggtc taggtaacct gtaaagaaag
HUBC4b   ********** ********** ********** ********** **********
HUBC4c   ..........  ..........  ..........  ..........  ..........
HUBC4d   ..........  ..........  ..........  ..........  ..........
HUBC4e   ..........  ..........  ..........  ..........  ..........
MUBC4    ********** ********** ********** ********** ****......
```

FIG. 12D

```
        900                                                    949
HUBC4a  gattaaaaat ttaagatgtt ctagttctgc tctctttgtt ttaaaaatca
HUBC4b  ********** ********** **........ .......... ..........
HUBC4c  .......... .......... .......... .......... ..........
HUBC4d  .......... .......... .......... .......... ..........
HUBC4e  .......... .......... .......... .......... ..........
MUBC4   .......... .......... .......... .......... ..........

950                                                    999
HUBC4a  ctgcttcaat ctacttcaaa agaaaaaaaa aacaataaaa agtgttgatg
HUBC4b  .......... .......... .......... .......... ..........
HUBC4c  .......... .......... .......... .......... ..........
HUBC4d  .......... .......... .......... .......... ..........
HUBC4e  .......... .......... .......... .......... ..........
MUBC4   .......... .......... .......... .......... ..........

1000
HUBC4a   a
HUBC4b   .
HUBC4c   .
HUBC4d   .
HUBC4e   .
MUBC4    .
```

FIG. 13A 1. 5'd-(GGCAGGTCTGTCTGCCAG)
2. 5'd-(GGTCTCTGCTCACACTTGCTG)
3. 5'd-(CAGCAAGTGTGAGCAGAGACC)
4. 5'd-(CTTTACAGGTTACCTAGACCAC)
5. 5'd-(GAAGCCAGCAACCAAAACCGA)
6. 5'd-(CACAAGCGAACGCCAGGC)
7. 5'd-(CCAGCCTGAGCACCCGCTT)
8. 5'd-(TAGGAGGCAGCTTTGGCTT)
9. 5'd-(CCAGCCTCGCCAATATGG)
10. 5'd-(GGTGTCTGAATGCACTGCA)
11. 5'd-(GCGGCCAGCAGGAGGCTGATG)
12. 5'd-(GTCTGAATGCACTGCACG)

FIG. 13B

| PCR primer set | UBC4 gene(s) amplified |
| --- | --- |
| (5) and (6), or (9) and (6) | HUBC4a |
| (8) and (6) | HUBC4b |
| (7) and (6) | HUBC4a, HUBC4b |
| (5) and (10) | HUBC4a, HUBC4c, HUBC4d, HUBC4e |
| (7) and (10) | HUBC4a, HUBC4b, HUBC4d |

FIG. 14

```
         .         .         .         .         .         .
gaagaaatatgcaattgtggaatgaaaaacttccgtaacttccaggtagatggagctaat   60
E  E  I  C  N  G  M  K  N  F  R  N  F  Q  V  D  G  A  N
         .         .         .         .         .         .
ttattgacttggcaagggcttattgttcctgacaaccctccatataagggggccttcaga  120
L  L  T  W  Q  G  L  I  V  P  D  N  P  P  Y  K  G  A  F  R
         .         .         .         .         .         .
atcgaaatcaactttccagcagagcacccattcaaaccaccgaagagcacacttaaagat  180
I  E  I  N  F  P  A  E  H  P  F  K  P  P  K  S  T  L  K  D
         .         .         .         .         .         .
ctgtcacccaaatgtccactaaaaggggcaggtctctctgccagtaaattagtgctgaaa  240
L  S  P  K  C  P  L  K  G  A  G  L  S  A  S  K  L  V  L  K
         .         .         .         .         .         .
actggaagccagcaaccaaaactgaccaagtaatccagtccctcacagcactggtgaatg  300
T  G  S  Q  Q  P  K  L  T  K  *
         .         .         .         .         .         .
acccccagcctgagcatccacttcaggctgacctagctgaataatactctaaggactgta  360
         .         .         .         .         .         .
aatatttctgtaagaatgctgaagtttacagagaaataggggggaaaagcgacttgtagac  420
         .         .         .         .         .
taaaatctgccacaattggctccagtaagtgtgagcagagaccc                  464
```

FIG. 15A

| Difference | Nucleotide(s) | Amino acid | Nature of difference |
|---|---|---|---|
| 1 | 295 | 14 | acc → ata<br>I → I (SILENT) |
| 2 | 296 | 15 | cgc → tgc<br>R → C |
| 3 | 301 | 16 | aaa → aat<br>K → N |
| 4 | 307 | 18 | ggg → gga<br>C → G |
| 5 | 320 | 23 | tgt → cgt<br>R → N |
| 6 | 326 | 25 | atc → tct<br>I → F |
| 7 | 334 | 27 | gtt → gta<br>V → V (SILENT) |
| 8 | 339 | 29 | gaa → gga<br>E → G |
| 9 | 392-394 | 47 | gat → DELETION<br>D → - |
| 10 | 412 | 53 | ata → atc<br>I → I |
| 11 | 434 | 61 | tac → cac<br>Y → H |
| 12 | 456 | 68 | atc → agc<br>I → S |
| 13 | 461 | 70 | ttt → ctt<br>F → L |
| 14 | 464-468 | 72 | aaaac → DELETION<br>FRAMESHIFT |
| 15 | 477 | N/A[a] | a → g |
| 16 | 487-488 | N/A[a] | ca → ag |
| 17 | 491 | N/A[a] | g → c |
| 18 | 493 | N/A[a] | g → t |
| 19 | 510 | N/A[a] | g → c |
| 20 | 519-520 | N/A[a] | ta → taa (INSERTION) |
| 21 | 529 | 92 | gct → gcc<br>A → A (SILENT) |
| 22 | 557 | N/A | c → t |
| 23 | 598 | 115 | ccc → ccg<br>P → P (SILENT) |

FIG. 15B

| Difference | Nucleotide(s) | Amino acid | Nature of difference |
|---|---|---|---|
| 24 | 604 | 117 | ccc → cct<br>P → P |
| 25 | 605 | 118 | aag → gag<br>K → E |
| 26 | 610 | N/A[a] | c → t |
| 27 | 614 | N/A[a] | g → a |
| 28 | 618 | N/A[a] | g → a |
| 29 | 635 | N/A[a] | g → t |
| 30 | 646 | 131 | aag → aac<br>K → N |
| 31 | 650 | N/A[a] | c → t |
| 32 | 656 | N/A[a] | a → t |
| 33 | 658 | N/A[a] | a → t |
| 34 | 676-677 | N/A[a] | ag → DELETION |
| 35 | 686 | N/A[a] | a → g |
| 36 | 694 | N/A[a] | t → g |
| 37 | 699 | 149 | a → DELETION<br>FRAMESHIFT |
| 38 | 704 | N/A[a] | c → t |
| 39 | 708 | N/A[a] | c → t |
| 40 | 712 | N/A[a] | g → a |
| 41 | 722 | N/A[a] | c → g |
| 42 | 729 | N/A[b] | g → a |
| 43 | 735 | N/A[b] | t → c |
| 44 | 741 | N/A[b] | c → t |
| 45 | 748 | N/A[b] | g → a |
| 46 | 756 | N/A[b] | a → g |
| 47 | 761 | N/A[b] | g → a |

DNA ENCODING UBIQUITIN CONJUGATING ENZYMES

This application is a 371 of PCT/GB95/00707, filed on Mar. 29, 1995.

The invention relates to a method for determining a predisposition for and diagnosing the existence of a degenerative disease, particularly, but not exclusively, Alzheimer's Disease (AD), and also products and processes for treating and obtaining treatments for such a degenerative disease. The single inventive concept also relates to products and processes for treating and obtaining treatments for Down's syndrome. In addition, the single inventive concept also relates to a method for determining a predisposition for and diagnosing the existence of cancer, particularly, but not exclusively, papilloma virus induced cancers, and also products and processes for treating and obtaining treatments for such cancers.

In the following application the term degenerative disease will be taken to mean a disease characterised by an aberration in the ubiquitination pathway and/or intermediate filament inclusion bodies of a diverse type such as those found in Parkinson's Disease, Pick's Disease, Alzheimer's Disease, as well as Rosenthal fibres in Cerebellar Astrocytomas, Cytoplasmic bodies in muscle and Mallory bodies in Alcoholic Liver Disease.

The degenerative neurological disease, Alzheimer's Disease, is one of the most challenging medical problems of our day. AD is a chronic, progressive, irreversible and fatal age-related dementia. It has received increased attention in recent years because of current demographic data, which data shows a continuously increasing proportion of elderly people within the population. The disease appears to be specific for humans and aged primates only and its causes are largeiy unknown. The disease presents a major public health problem in that caring for demented patients is particularly demanding on health care resources.

Studies of the disease are complicated by the fact that a reliable diagnosis depends on analysis of brain tissue, suicIh diagnosis usually being conducted post-mortem and being of no use to the patient concerned. Putative clinical diagnosis is made principally bv exclusion of other causes of dementia—a largely unsatisfactory situation.

Studies are further hindered by the fact that useful animal or cell models are not yet available for investigation. Hence the development of therapeutic agents for treating the disease is not vet possible.

An understanding of the disease is further complicated by the fact that in some cases AD is familial, whereas in other cases it is sporadic. However, in all instances post-mortem diagnosis is determined by the distinctive neuropathological features of the disease. These features comprise two conspicuous types of deposits; amyloid plaques and neurofibrillary tangles (NFTs). The plaques consist of aggregates of a peptide derived from amyloid precursor transmembrane protein (APP). The plaques are generated by abnormal protein metabolism. NFTs and their constituents, the paired helical filaments (PHFs) consist largely of a microtubular-associated protein, known as tau, in various abnormal states of phosphorylation. It is known that PHFs are very highly insoluble and this makes their analysis and characterisation extremely difficult. In addition, it is known that NFTs are associated with the protein ubiquitin; however, the significance of this association is unknown. That ubiquitin is a component of paired helical filaments was first disclosed in 1987. It is also known that ubiquitin is a common factor in intermediate filament inclusion bodies of a diverse type in man such as those found in Parkinson's Disease, Pick's Disease, Alzheimer's Disease as well as Rosenthal fibres in Cerebellar Astrocytomas, cytoplasmic bodies in muscle and Mallory bodies in Alcoholic Liver Disease. However, the significance of these associations is unknown.

It is also interesting to note that the pathology of AD is also found in victims of Down's syndrome. The significance of this will be described in greater detail hereinafter.

It is, however, known that the ubiquitination pathway functions to target cellular proteins for degradation. The pathway is thought to operate in all cell types and is necessary for cell viability. Ubiquitination is particularly important in the control of: proliferation and differentiation; DNA repair; heat shock response; and organelle formation. A functional de-ubiquitination system is also necessary for cell viability. Short half-life proteins such as those which control progress through the cell cycle are targeted for degradation by ubiquitination. Abnormal and mutant proteins are processed in a similar way. It is of note that many proteins are resistant to proteolytic digestion in the absence of ubiquitination. Despite the possible involvement of ubiquitin in degenerative disease pathology and its importance in protein processing, there is no prior art describing the role of ubiquitin associated enzymes and, in particular, ubiquitin conjugating enzymes in degenerative diseases and in particular in AD.

Moreover, four human ubiquitin conjugating enzymes have been discovered but it is of note that none of these enzymes maps to a chromosome region hitherto implicated in degenerative diseases and in particular in Alzheimer's Disease (5, 6, 7).

The ubiquitination pathway involves a cyclical four step process. The process includes a number of enzymes such as: ubiquitin activating enzymes (E1), ubiquitin conjugating enzymes (E2 or UBC), ubiquitin-protein ligases (E3) and proteosomes but, as mentioned, there is no suggestion in the prior art that any of these enzymes has a role to play in degenerative disease and in particular in Alzheimer's Disease.

In order that the invention may be understood the ubiquitination pathway will be described in greater detail.

In the following description enzymes E1, E2 (or UBC) and E3 prefixed with the letter H, for example HUBC4, represent the human version of the relevant enzyme such as human ubiquitin conjugating enzyme and enzymes E1, E2 (or UBC) and E3 without this prefix for example UBC4 represent the yeast version of the relevant enzyme such as yeast ubiquitin conjugating enzyme.

It is known that the ubiquitination pathway has a major role to play, at least, in the selective degradation of normal and short-lived proteins such as those that control progress through the cell cycle for eg p53 (8). The pathway firstly involves activation of ubiquitin by the enzyme E1 in at ATP-dependent manner. Activation involves the formation of a thioester between the active cysteine residue of E1 and the C-terminal glycine of ubiquitin. Once activated, the ubiquitin is transferred to a cysteine residue of a ubiquitin-conjugating enzyme (such as UBC4 or HUBC4). The ubiquitin-conjugating enzyme then catalyses the formation of an isopeptide bond between the C-terminal glycine of ubiquitin and the E-amino group of a lysine residue on a target protein. This is brought about by E3 ubiquitin ligases specifically binding to target proteins that are not otherwise recognised by E2's. In addition, ubiquitin also becomes conjugated to itself via a lysine residue at position 48 of ubiquitin resulting in the formation of multiubiquitin chains.

Multiujbiquinated proteins serve as targets that are recognised and degraded by an ATP-dependent protease complex.

The ubiquitin-conjugating enzymes or E2's comprise a family of proteins characterised by a highly conserved catalytic site. In yeast at least 10 different E2's have been identified. A number of these E2's, such as UBC1, UBC4 and UBC5 play an important role in the specific targeted breakdown of abnormal and short-lived proteins.

Another fraction of E2's catalyse the transfer of ubiquitin to small proteins, such as histones, in a reaction that does not require E3. These reactions result in monoubiquitin derivatives that do not serve as proteolysis intermediates.

It is of note that in yeast the ubiquitin conjugating enzymes (E2) UBC4 and UBC5 show a 92% protein sequence homology and mutation in both these genes is required for a substantial reduction in growth rates. In addition, over expression of UBC1 complements UBC4 and UBC5 mutations in yeast. It would therefore seem that these enzymes have significant structural and functional similarities and in view of these facts we consider that both the functionally equivalent human ubiquitin conjugating enzymes HUBC5 and HUBC1 have likewise a significant role to play in the diagnosis and treatment of the diseases described herein. For example, it may be that a mutation or polymorphism in HUBC4 will be complemented by a mutation or polymorphism and/or over expression of HUBC5 and/or similarly, a mutation or polymorphism and/or over expression of HUBC1.

It may be that an aberration in any one of the human ubiquitin conjugating enzymes results in the diseases described herein.

The ubiquitination pathway also has relevance in the control of cell growth or cell division and thus abberations in this control are typically characterised by cancerous growths and particularly papilloma virus induced cancerous growths. This has been realised as a result of the following information.

It has recently been reported that ubiquitin-conjugating enzymes are involved in ubiquitination of p53 (1,2,3).

p53 is involved in the cell cycle and more specifically it is a $G_1$-S checkpoint protein. During the cell cycle the cell enters a number of defined stages termed $G_1$, where the cell prepares for replication, S, where cellular DNA is replicated, $G_2$ an interval prior to cell separation, and M, where the cell divides. During $G_1$, p53 essentially checks the integrity of the cell and if mutations in the DNA are identified p53 prevents commencement of S phase and so prevents cell replication. In this way, p53 ensures that abberations in cellular DNA are not propagated by cell division. It therefore follows that p53 is an important cellular protein, indeed, it has been termed a tumour suppressor protein. Multi-ubiquitination of this protein therefore targets it for destruction and removes from the cell an important control agent.

Since the agent responsible for ubiquitination of p53 is a ubiquitin conjugating enzyme it follows that mutations in this enzyme which deleteriously affect cellular levels of p53 will have a role to play in tumour formation.

In addition, over expression of the human ubiquitin-conjugating enzyme active against p53, will have deleterious consequences.

Abberations in p53 control are known to be associated with cancers caused by the human papilloma virus (HPV) and specifically types 16 and 18 which appear to stimulate the ubiquitin-dependent degradation of the p53 tumour suppressor protein.

HPV-16 and HPV-18 are typically associated with malignant legions such as cervical cancer and head and neck cancer. These two HPV types are referred to as high risk HPV's as opposed to low-risk HPV's which are generally associated with benign lesions. Both of the high-risk HPV's encode proteins, termed E6 and E7, which bind to cellular regulatory proteins. Specifically E6 binds to a cellular protein of 100KDa, termed E6-associated protein (E6-AP). This E6-E6-AP complex binds p53 and so enables a ubiquitin-conjugating enzyme to ubiquitinate p53. It would therefore seem that E6 when bound to the E6-associated protein, acts as a ubiquitin protein ligase or E3.

It would therefore seem that the human papilloma virus is adapted to make use of the cellular ubiquitination pathway and so overcome the $G_1$-S checkpoint which prevents replication of aberrant DNA.

It has recently been reported that it is possible to ubiquitinate p53 in the absence of E6. Indeed, a novel rabbit ubiquitin conjugating protein, designated E2-F1, has been described in the ubiquitination of non-"N-end rule" substrates such as glyceraldehyde-3-phosphate dehydrogenase and p53. (4)

We consider therefore that a HUBC4 is recruited by the E6-E6-AP/p53 complex in HPV 16 or 18 affected cells with the result that p53 is ubiquitinated more rapidly than in normal cells and thus is more rapidly degraded.

This results in the infected cell behaving as if it has lost p53 function. Mutations in the p53 gene resulting in the loss of functional p53 are well known to result in a malignant phenotype. Thus we believe that agents which either interfere with the interaction between E6-E6-AP and a HUBC4 or with the interaction between E6-E6-A6/HUBC4 complex and p53 would function as treatments for HPV induced cancers for example, cervical cancers. We also believe that antagonists of the HUBC4 enzyme will also function as treatments for HPV infected cells and HPV induced cancers.

We also consider that abberations, polymorphisms or mutations in the HUBC4 gene may have a part to play in the inappropriate or excessive ubiquitination of p53 and thus in the untimely removal of an important means of cellular control and the development of unregulated cell division.

In some instances, a degenerative disease such as for example Alzheimer's Disease is familial. It is therefore logical to suppose that the gene or genes relating to these familial diseases such as Alzheimer's Disease are located on particular chromosomes. To this end, a number of genetic investigations have been undertaken. Investigations relating to AD will now be summarized.

It has been found that familial AD appears to segregate as an autosomal dominant trait. In some families mutations in the amyloid precursor protein (APP) have been described. For example mutations at amino acid 670, 671, 692, 693 or 771 of this protein have sometimes been found to segregate with AD in families. The APP gene is located on human chromosome 21 at location 21q21.3 and was initially seen as a particularly attractive candidate gene for giving rise to Alzheimer's Disease because patients with Down's syndrome (chromosome 21 trisomy dysfunction) often show the pathological features of AD when their brains are examined at autopsy. However, the proportion of familial AD cases associated with mutations in the APP gene on chromosome 21 is small. In general, the APP mutations described to date involve conservative amino acid changes which a priori would not be predicted to exert a major effect on the behaviour of the resultant protein.

Other workers have described pedigrees segregating senile onset familial Alzheimer's Disease and suggested an association with genetic markers on chromosome 19q. However, once again the number of families falling into this category is relatively small.

A large number of genetic studies have recently suggested that a gene responsible for familial AD maps to human chromosome 14 and in particular 14q24.3. Indeed, there has also been some suggestion that the gene on human chromosome 14 may in fact also be playing a role in the families where linkage to chromosome 21 is suspected. The individuals who have established this genetic linkage have speculated about genes known to lie on human chromosome 14 and their potential involvement in the pathology of AD. Such genes include the protease inhibitors AACT, PI, the protease Cathepsin G and TGFβ3. In addition, the transcription factor c-FOS maps to the 14q24 region of chromosome 14. There has been speculation on the possible role of c-FOS because this transcription factor may be involved in the transcriptional regulation of the APP gene. However, the significance of this in Alzheimer's Disease remains unestablished. Furthermore, the 70 KDa heat shock protein HSPA2 also maps to the 14q24 region of chromosome 14. The product of this gene is a molecular chaperone potentially involved in protein folding and assembly and could thus act theoretically in APP processing so that mutations would possibly lead to later amyloid deposition. However, once again there is no evidence to suggest that this hypothesis is true in AD.

In conclusion, the prior art is confusing in that it suggests that there are any number of genetic influences on the development of familial AD. What is clear, however, is that to date, individuals skilled in the art have not been able to quickly isolate the genes involved in AD and particularly familial AD.

In addition, the genes involved in the other herein referred to degenerative diseases and cancers have also not been isolated.

Our investigations have led us to identify a surprising number of genes located on a number of chromosomes but coding for almost identical, or at least very similar proteins, which proteins would seem to be ubiquitin conjugating enzymes. One gene maps to human chromosome 14 at location 14q24.3. This gene has never previously been described. We have called this gene and the protein it encodes human ubiquitin conjugating enzyme 4 (HUBC4, and more specifically HUBC4a). Our investigations have also lead us to identify other genes that code for human ubiquitin conjugating enzymes which genes map to: human chromosome 22 at location 22 q12-13, human chromosome 12 at location 12 p and human chromosome 19 and human chromosome 13. These genes have never previously been described. Surprisingly all these genes encode for human ubiquitination enzymes specifically enzymes identical to or variants of HUBC4a. We have called these genes HUBC4b, HUBC4c and HUBC4d and HUBC4e, respectively.

Experiments have shown that a rabbit protein is active as a ubiquitin carrier protein in rabbit reticulocyte lysates (4). Partial sequencing of tryptic digestion fragments from this protein are homologous to fragments of the protein encoded by our HUBC4b gene. Thus it can be suggested that a rabbit protein related to our HUBC4b gene product has a part to play in the cellular ubiquitination pathway in that species and so it is likely that the HUBC4b gene product and the variants thereof hereindescribed equally have a part to play in the human cellular ubiquitination pathway.

The genes which we have therefore successfully identified are likely to form part of the cellular ubiquitination pathway and are typically likely to be involved in targeting cellular proteins for degradation. Since it is known that proteins are resistant to proteolytic digestion in the absence of ubiquitination it is not surprising that mutations in the genes encoding the enzymes which are part of the ubiquitination process can lead to an increase in protein half-life within the cell and corresponding deleterious consequences such as an inability to complete the normal cell cycle. Indeed, we believe that mutations in either the ubiquitination pathway or the target protein for ubiquitination in human tissues result in pathological consequences. Mutations in the ubiquitination enzymes and in particular in the herein described class of HUBC4 enzymes lead to decreased or enhanced protein ubiquitination. The former variant may affect cell proliferation and may also be involved in generation of intermediate filament inclusion bodies of different types in several major human diseases and in particular in Alzheimer's Disease. The latter variant may affect cell growth control and so lead to cancerous growths.

Having identified the HUBC4 class of genes we have now provided a human cDNA, named HUBC4b, which encodes a protein of 154 amino acid residues having a molecular weight of 17.9 KDa and that demonstrates a 55% homology in primary sequence, and also displays a similar hydrophobicity profile, to that of the yeast E2 gene UBC4. The key cysteine residue thought to become involved in thioester bond formation and specific adjacent amino acids are conserved. It is of note that there is no prior art teaching that a human homologue of the yeast UBC4 gene or corresponding protein might have any role or relevance in degenerative diseases and in particular in AD. Indeed, human homologues of yeast UBC genes have been said to have a role to play in DNA repair, DNA replication, G1-S cell cycle progression and G2 check point progression. Hence this prior art teaching tends to lead away from the hypothesis that ubiquitin conjugating enzymes, as a class, might have an important role to play in AD or other diseases and makes our suggestion that the HUBC4 class of genes is involved in degenerative diseases, and in particular in AD, all the more unexpected.

The cDNA for any of the HUBC4 class of genes or any single one of these genes including genetic control elements and introns may be used for gene therapy approaches using nucleic acid delivery vectors (viruses, liposomes, etc) and methods for achieving tissue-specific expression which are known to the skilled man. Provision of a cDNA clone from any of the aforementioned genes and the genomic DNA sequence as well as Yeast Artificial Chromosomes containing any one of the entire genes will allow the sequence of introns at the intron-exon boundaries to be determined by methods well-known to the skilled man. The availability of this data allows a number of well-known technologies for the detection of mutations to be applied, for example, but not limited to, SSCP (5). Thus we provide DNA sequence data which will allow the identification of polymorphisms and/or mutations in the class of human HUBC4 genes and so aid in the diagnosis of degenerative diseases such as familial AD and/or sporadic AD and also in the diagnosis of a vulnerability to, at least, human papilloma virus induced cancer. The sequences defined for the first time herein will allow the development of diagnostic tests for mutations either at the DNA or RNA level again using methods known to the skilled man such as PCR for example using the "ARMS" technique (6).

In summary therefore, our invention concerns the identification of genes which we call HUBC4a, HUBC4b, HUBC4c, HUBC4d and HUBC4e, mutations in which we believe are responsible, at least, for the degenerative diseases described herein and cancers in particular papilloma virus induced cancers.

Our invention is consistent with observations made in the prior art such as: the fact that familial AD is thought to involve a gene on chromosome 14 at location 14q24.3 and one of our genes maps to this location; that mutations at this locus are consistently found to segregate with Alzheimer's Disease in pedigrees; and that ubiquitin is well-known to be involved in protein degradation and that therefore ubiquitin conjugating enzyme anomalies may result in the inappropriate accumulation of protein deposits and disease and/or a lack of cell growth control.

We speculate that mutant forms of ubiquitin conjugating enzymes show variable activity when functioning as ubiquitin conjugating enzymes. Over many years this leads to alterations in the rates of protein processing particularly in the CNS and eventually leads to the build tip of intermediate inclusion bodies such as NFTs and/or amyloid plaques.

We also provide the sequence of cDNA for a ubiquitin conjugating enzyme in the mouse (mUBC4b). The availability of this sequence will allow genomic clones for the corresponding mouse ubiquitin conjugating enzyme to be isolated, again using well-known methods. The availability of such mouse sequence will allow transgenic mice to be prepared using established technologies where the function of this enzyme is either destroyed by gene knockout or modified by the introduction of specific mutations. In this fashion, mouse animal models will be created which develop symptoms characteristic of degenerative diseases such as AD homologous to the condition in man; and/or models will be created which are susceptible to cancers and in particular papilloma virus induced cancers. Any compound which delays or prevents the appearance of the pathological features of these diseases in such transgenic animals is likely to have therapeutic benefit in man.

We also provide herein the predicted protein sequences of human ubiquitin conjugating enzymes HUBC4a, HUBC4b and HUBC4c from human chromosome 14, 14q24.3; human chromosome 22q; and human chromosome 12p, respectively. These proteins themselves may have therapeutic uses.

Of particular value are monoclonal or polyclonal antibodies raised using standard techniques either to the whole protein, to epitopes or fragments thereof, to truncated variants thereof, to splicing variants thereof and to protein variants displaying mutation and amino acid changes. Such variants will be identified as described above by, for example but not limited to SSCP analysis (5) of the DNA from affected patients. Antibodies such as these will have utility in establishing the diagnosis of degenerative diseases such as, but not limited to, AD in post-mortem samples and may facilitate analysis of neurological biopsies.

In addition, these antibodies may be usefully employed to block selected HUBC4 enzymes in order to prevent or at least mitigate p53 degradation.

We also consider that our invention has important implications for the treatment of Down's syndrome. We base this statement on the following facts. An individual who has either a mutant or polymorphic variant of one of the genes for HUBC4 and/or APP exhibits AD. In these circumstances, the balance between functional HUBC4 and APP is impaired. We consider that the balance between the HUBC4 and APP gene products is necessary to prevent disease.

For example, in a normal diploid individual the gene complement is as follows:

| HUBC4 | APP |
|---|---|
| HUBC4 | APP |

Whereas in an individual suffering from AD, any one or more of the above genes is defective resulting either in insufficient functional HUBC4 gene product and/or deposition of APP gene product. Similarly, in a sufferer of Down's syndrome this balance is impaired, but for different reasons. A sufferer of Down's syndrome has an extra chromosome 21 and the individual's gene complement is as follows:

| HUBC4 | APP |
|---|---|
| HUBC4 | APP |
|  | APP |

This imbalance brings about the pathological features, characteristic of AD, in sufferers of Down's syndrome. It follows therefore that one way of redressing the balance is to provide a Down's syndrome sufferer, via the technique of the invention, with additional HUBC4 gene or gene product.

It is therefore the object of the present invention to provide a method which enables a determination of a predisposition for and diagnosis of degenerative diseases such as AD; also products and processes for treating and obtaining treatments for a degenerative disease such as AD and Down's syndrome; and also a method which enables a determination of a predeposition for cancers, particularly, but not exclusively papilloma virus induced cancers, and also products and processes for treating and obtaining treatments for such cancers.

According to a first aspect of the invention there is therefore provided genetic material having, including or derived from, substantially the genetic sequence structure shown in FIG. 1, or part thereof, or a functionally equivalent or functionally related or associated nucleotide sequence.

In an alternative embodiment of the invention the genetic sequence structure comprises a nucleotide substitution at nucleotide 320 and ideally a thymine to cytosine base substitution.

In yet a further alternative embodiment of the invention said genetic sequence structure comprises a nucleotide substitution at nucleotide 605 and ideally an adenine to guanine substitution.

We consider that the said genetic sequence structure without any of the aforementioned substitutions represents the genetic sequence structure of the ubiquitin conjugating gene HUBC4a. Tie genetic sequence structure including the said substitutions represents the coding sequence structure of the ubiquitin conjugating gene HUBC4b.

In yet further preferred embodiments of the invention said genetic sequence structure may include any one or more of the variations shown in FIG. 5.

According to a second aspect of the invention there is provided a protein. ideally a ubiquitin conjugating enzyme, having substantially the amino acid sequence structure shown in FIG. 1, or part thereof, or a functionally equivalent or functionally related or associated amino acid sequence structure.

In an alternative embodiment of the invention said amino acid sequence structure comprises an amino acid substitution at position 23 and ideally a cysteine to arginine substitution.

In yet a further alternative embodiment of the invention said amino acid sequence structure comprises a substitution at position 118 and ideally a lysine to glutamic acid substitution.

We consider that the amino acid sequence structure without any of the aforementioned substitutions represents the sequence structure of the protein encoded by the gene HUBC4a and that the amino acid sequence structure including the aforementioned substitutions represents the amino acid sequence structure encoded by the gene HUBC4b.

In yet alternative embodiments of the invention said amino acid sequence structure may include any one or more of the variations shown in FIG. 15.

For the avoidance of doubt, DNA sequences of the invention include sequences useful in securing expression in prokaryotic or eukaryotic host cells of a polypeptide as hereinbefore defined. DNA sequences of the invention are specifically seen to compromise:

a) a DNA sequence set forth in FIG. 1 and fragments or variants thereof, and in particular the fragments which code for the polypeptide of FIG. 1, or its complimentary strand;

b) a DNA sequence which hybridises to the DNA sequence set forth in FIG. 1 or to fragments or variants thereof; which sequence by implication shows at least 30% and preferably 50°% homology with said FIG. 1 sequence or fragments; such a sequence includes but is not restricted to the primers hereindescribed.

c) a DNA sequence which, but for the degeneracy of the genetic code, would hybridise to the DNA sequence set forth in FIG. 1 or to fragments or variants thereof and in particular to the fragments or variants which code for the polypeptide of FIG. 1.

Specifically comprehended in part b) are genomic DNA sequence encoding allelic variant forms of the polypeptide of FIG. 1. Specifically comprehended in part c) are manufactured DNA sequences. Manufactured sequences may readily be manufactured according to the methods of, for example, Edge et al, *Nature*, 292, 756–762 (1981).

The degeneracy of the genetic code allows substantial freedom in the choice of codons which can be used to construct a gene for the appropriate polypeptide of the present invention. Codons are normally selected which are preferred by the host.

Polynucleotide probes may be constructed which are capable of hybridisation to any portion of the aforementioned DNA sequence or of a corresponding RNA or cDNA sequence. It will be appreciated that the nucleotide probe will comprise a nucleotide sequence capable of hybridisation to a sufficient length of the sequence to be determined to ensure that the probe unambiguously detects the sequence of interest. In general, the probe will be capable of hybridising to at least eight consecutive nucleotides of the sequence to be determined.

According to a third aspect of the invention there is provided a polynucleotide which comprises a nucleotide sequence capable of hybridising, to a DNA sequence as hereinbefore defined or a fragment thereof, or a corresponding RNA sequence, said probe optionally having a labelled or marker component. Preferably said probe comprises at least one probe as illustrated in FIG. 13 or a substantially similar probe having deletions or additions which do not prevent the probe from hybridising to said DNA sequence.

According to a fourth aspect of the invention there is provided at least one antibody, monoclonal or otherwise, raised against a whole or a part of the DNA sequence structure or amino acid sequence structure shown in FIG. 1.

In a preferred embodiment of the invention said antibodies are raised against either a highly conserved region of the DNA sequence structure encoding for amino acids 60–90 or more preferably 72–88, shown in FIG. 1, or alternatively, against amino acids 60–90 or more preferably 72–88, shown in FIG. 1.

Ideally said antibodies are raised against the C terminal amino acids and more preferably amino acids 137 to 154.

Such antibodies or probes may be used to detect the presence or indicate the absence of a polypeptide as hereinbefore defined or corresponding DNA or RNA as appropriate and hence the presence or absence of material possessing ubiquitin conjugating enzyme activity. Thus the probes or antibodies may be used to indicate whether an altered ubiquitin conjugating enzyme mediated condition may be at least partly caused by an absence of ubiquitin conjugating enzyme HUBC4 activity.

According to a fifth aspect of the invention there is provided a delivery means including a whole or a part of the DNA sequence structure and/or the amino acid sequence structure shown in FIGS. 1, 2a or 14.

According to a sixth aspect of the invention there is provided genetic material having, including or derived from substantially the mouse genetic sequence structure shown in FIG. 3, or part thereof, or a functionally equivalent or functionally associated nucleotide sequence.

According to a seventh aspect of the invention there is provided a protein having substantially the amino acid sequence stricture shown in FIG. 4, or part thereof, or a sequence structure which encodes for a protein functionally identical or similar to the protein shown in FIG. 4.

According to a eighth aspect of the invention there is provided at least one antibody, monoclonal or otherwise, raised against a whole or a part of the DNA sequence structure, or amino acid sequence stricture, shown in FIGS. 3 and 4 respectively.

According to an ninth aspect of the invention there is provided a delivery means including a whole or a part of the DNA sequence structure and/or amino acid sequence structure shown in FIGS. 3 and 4 respectively.

In a preferred embodiment of the invention the aforementioned delivery means comprises a vector, ideally a replicative vector. Alternatively, in another embodiment of the invention the delivery means comprises a liposome. Alternatively, said delivery means is a plasmid.

In a preferred embodiment of the invention said delivery means is a retroviral vector which enables specific delivery of the DNA sequence structure to tissues for the purpose of gene therapy.

In yet a further preferred embodiment of the invention the delivery means is a adenoviral vector.

In yet a further preferred embodiment of the invention the delivery means is a Herpes virus vector.

It will also be evident to those skilled in the art that monoclonal or polyclonal antibodies raised using standard techniques either to the whole protein encoding any one of the HUBC4 proteins herein described or to epitopes or fragments thereof, to truncated variants thereof, to splicing variants thereof and to protein variants displaying mutations or amino acid changes may be produced. In addition, antibody fragments, which preferably contain the binding region of the antibody, as well as chimeric antibodies, for example as described in GB 2188638 may also be used. In the instance where fragments are used such fragments may be Fab-type fragments, ie fragments lacking an Fc portion such as Fab, Fab 1 and F(ab1)2 fragments or so called "half molecule" fragments obtained by reductive cleavage of the disulphide bonds connecting the heavy chain components in an intact antibody.

Further, secondary antibodies may also be raised to the said aforementioned antibodies.

Antibodies such as the above will have utility in establishing the diagnosis of AD in post-mortem samples and may facilitate analysis of neurological biopsies or other fluid/tissue samples. Moreover, given the known implication of ubiquitination in a variety of other human diseases, these antibodies may prove valuable in the diagnosis of Parkinson's Disease, Alcoholic Liver Disease, Pick's Disease and Cerebellar Astrocytomas.

Antibodies such as the above will also have utility in blocking the activity of at least one selected ubiquitin conjugating enzyme and so safeguard against, at least, the deleterious ubiquitination of p53 particularly in, but not limited to, HPV infected cells and cancers.

Ideally, the afore referred to delivery means comprise agents, such as antibodies that block the activity of HUBC4, and particularly, but not exclusively, HUBC4b and/or HUBC4b complexes.

Moreover, said antibodies may prove valuable in monitoring the level of HUBC4 expression in individuals receiving gene replacement therapy according to the invention to treat any of the diseases described herein. Selective monitoring of the different sorts of HUBC4 forming the HUBC4 classes herein described can be undertaken by manufacturing antibodies which recognise differences in the proteins encoded by the HUBC4 genes.

An alternative method of blocking or reducing the synthesis of HUBC4 proteins comprises use of antisense sequences relating to the whole or a part of the DNA sequences shown in FIGS. 1, 2 or 14.

According to a tenth aspect of the invention there is provided a non-human transgenic animal whose genetic material includes at least one copy of the DNA sequence structure shown in FIGS. 1, 2 or 14 and/or at least one mutation or polymorphic variant of the DNA sequence structure shown in FIGS. 1 or 2 or 14 or alternatively, a non-human transgenic animal whose genetic material does not include a part of the DNA sequence structure shown in FIG. 3 such that the protein encoded by said sequence structure is either non-functional or not expressed.

Alternatively there is provided a non-human transgenic animal whose germ cells and somatic cells contain at least one copy of the DNA sequence structure shown in FIGS. 1, 2 or 14 and/or at least one mutation or polymorphic variant of the DNA sequence structure shown in FIGS. 1 or 2 or 14; and/or a recombinant activated mutant form of the DNA sequence structure shown in FIGS. 1 or 2 or 14, provided in said animal at an embryonic stage, and/or an absence of the DNA sequence structure shown in FIG. 3 such that the protein encoded by the sequence structure is either non-functional or not expressed, and its offspring possessing the same gene sequence.

Preferably said transgenic comprises multiple copies of said sequence structure and/or attachment of said sequence structure to a promoter, inducible or otherwise, that provides for enhanced expression of said sequence structure. More preferably said transgenic comprises a reporter gene so that temporal and/or spatial expression of said sequence can be monitored. Ideally said reporter gene encodes a visual marker.

In a preferred embodiment of the invention said non-human transgenic animals are provided using the YACs hereinafter described.

In a preferred embodiment of the invention said animal is a rodent such as a mouse or a rat.

According to an eleventh aspect of the invention there is provided offspring of said transgenic animal.

It will be evident to those skilled in the art that the availability of transgenic animals will allow for animal models that develop degenerative diseases such as AD homologous to the condition in man and also animal models that are susceptible to cancers and in particular papilloma virus induced cancers. These models can be used to identify treatments that prevent the onset or continuance of degenerative diseases such as AD in transgenic animals and which are therefore likely to have therapeutic benefit in human AD and also treatments which can delay, prevent or treat cancers such as papilloma virus induced cancers.

According to a twelfth aspect of the invention there is provided a method of diagnosing a predisposition for, or the existence of, a degenerative disease such as Alzheimer's Disease comprising a comparison of test DNA sequence structure from an individual to be tested with the sequence structure shown in FIGS. 1, 2 or 14, or parts thereof.

In a preferred method of the invention the method comprises a comparison of test DNA sequence structure from human chromosome 14, and ideally location 14q24.3 of human chromosome 14, from an individual to be tested with the DNA sequence structure, or part thereof, shown in FIG. 1 and/or including/excluding, respectively, the above mentioned substitutions.

According to a thirteenth aspect of the invention there is provided a method for diagnosing a predeposition for, or susceptibility to, cancers, and in particular papilloma virus induced cancers comprising a comparison of test DNA sequence structure from an individual to be tested with the DNA sequence structure shown in FIGS. 1, 2 or 14, or parts thereof.

In a preferred method the diagnosis involves a comparison of test DNA sequence structure from human chromosome 22 and ideally location 22 q of human chromosome 22, from an individual to be tested with the DNA sequence structure, or part thereof, shown in FIG. 1 and/or including/excluding, respectively, the above mentioned substitutions.

Preferably a type of HUBC4 cDNA sequence and the corresponding type of HUBC4 genomic sequence are used in concert for the identification of variations in a sample from an individual to establish whether that sample contains mutant forms of the different HUBC4 sequences. In a preferred aspect of the invention the existence of a mutation or polymorphic variation is determined by single strand conformational polymorphism analysis. In a more preferred aspect of the present invention, mutation or polymorphic variation is detected by any method known in the art for the identification of mutation or polymorphic variation in DNA sequences including direct DNA sequencing (7 and 8).

In a further aspect of the present invention, diagnosis of the presence of a particular mutation or mutations in the HUBC4 genes may conveniently be affected by PCR based techniques such as the ARMS method (6) for assessing the presence of a point mutation. Such point mutations are identified by the approaches described above.

It will also be evident to those skilled in the art that the method of diagnosis essentially involves detection of the presence or absence of a mutant HUBC4 allele in a sample from an individual (an allele is defined as a variant of a genetic locus and is inherited according to conventional principles of genetic segregation).

Variation of a genetic locus may be identified using DNA sequence variation or any other method known in the art for detecting variation at a genetic locus including the analysis of microsatellite regions or minisatellite regions or restriction fragment length polymorphism (RFLP). The method of the invention may also be performed using any expressed gene product such as the HUBC4 protein or RNA.

It is also within the scope of the invention to express the protein whose sequence structure is shown in FIGS. 1, or 14 in either prokaryotic or eukaryotic heterologous expression systems.

According to a fourteenth aspect of the invention there is provided a recombinant DNA sequence identical or substantially similar to the sequence shown in FIGS. 1 or 3, or any part thereof. Ideally said sequence shown in FIG. 1 includes the aforementioned substitutions.

According to a fifteenth aspect of the invention there is provided an expression and ideally export system, such as for example a yeast, bacterial or mammalian cell, which is capable of expressing and ideally also exporting the gene and protein products respectively of the invention.

In a preferred embodiment of the invention said system includes multiple copies of the said gene and/or an enhanced promoter whereby expression of the said gene product is enhanced. It will be apparent to those skilled in the art that such a system could be used for therapies based on surgical transplantation of cells into critical loci preferably neuronal loci.

It will be appreciated that where the desired product is not passed out of the host cell at a commercially useful rate, the host cell may be cultured and harvested as the intact cell and the desired polypeptide recovered by subsequently extracting the cells, for example after separation from the medium containing nutrients necessary for growth of the host cell. Where the product is passed out of the host cell into the surrounding culture solution, then the polypeptide may be recovered by extraction in the normal way.

According to a sixteenth feature of the present invention there is therefore provided a transformed host capable of expressing a polypeptide as hereinbefore defined, the host comprising a replicable plasmid-derived expression vehicle, said vehicle comprising genetic material coding for the said polypeptide.

According to a seventh aspect of the invention there is provided recombinant host cells transformed with the expression system of the invention. Said recombinant host may be a prokaryotic or a eukaryotic host such as embryonic stem cells or mammalian cells.

According to an eighteen aspect of the invention there is a provided a method of producing a human ubiquitin conjugating enzyme of the invention which method comprises culturing a recombinant host cell transformed with the one of the HUBC4 expression systems of the invention.

According to an nineteenth aspect of the invention there is provided the DNA sequence structure and the protein sequence structure shown in FIGS. 1, 2 or 14, or any part thereof, for the treatment of degenerative diseases such as Alzheimer's Disease, or Down's syndrome.

In a preferred embodiment of the invention said amino acid sequence structure shown in FIGS. 1, 2 or 14 is provided in a pharmaceutical composition in association with a pharmaceutical excipient or carrier.

According to a twentieth aspect of the invention there is provided a method of treating a degenerative disease such as Alzheimer's Disease using the DNA and/or protein sequence structures, or any parts thereof, shown in FIGS. 1, 2 or 14.

According to a twenty-first aspect of the invention there is provided a method of treating Down's syndrome using the DNA and/or protein sequence structures, or any parts thereof, shown in FIGS. 1, 2 or 14.

The polypeptides, and fragments thereof, of the present invention are obtainable in a biologically pure and homogenous form. The present invention also provides a polypeptide as herein defined unaccompanied by associated native glycosylation. In addition to polypeptides as hereinbefore defined, the present invention also embraces other products which possess enzymic activities as human ubiquitin conjugating enzymes such as polypeptide analogues or other members or the family of human ubiquitin conjugating enzymes which may be capable of substituting for HUBC4 or working with, the polypeptides of FIGS. 1, 2 or 14, in vivo or in vitro.

These polypeptide analogues include polypeptides which differ from that hereinbefore defined in terms of the identity or location of one or more amino acid residues. For example, such analogues may contain substitutions or terminal or intermediate additions or deletions of such residues. Such analogues would share ubiquitin conjugating enzyme activity. As examples, projected products of the invention include those which are more stable to hydrolysis (and therefore may have more pronounced or longer lasting effects than naturally occurring); or which have one or more cysteine residues deleted or replaced by, for example, alanine or serine residues and are potentially more easily isolated in active form from microbial systems.

According to a twenty-second aspect of the invention there is provided a protein or polypeptide having the sequence stricture shown in FIGS. 1, 2, 14 or 3, or parts thereof, or a homologue or analogous thereof.

The polypeptides of the present invention may conveniently be prepared by genetic engineering techniques. Analogues of the present invention may be prepared by expression of genes coding for such analogies. Such genes may readily be obtained by modifications of cDNA and genomic genes by well-known site directed mutagenesis techniques.

According to a yet further aspect of the present invention there are provided Yeast Artificial Chromosome (YAC) clones and/or cosmid clones which contain the class of HUBC4 genes herein described plus their genetic control elements including promoters and enhancers.

In a further aspect of the present invention highly polymorphic microsatellite repeats are isolated from within these YAC and/or cosmid clones for use in diagnosis of degenerative diseases such as AD in families.

It is of note that AD does not naturally occur in rodents and indeed in our own investigations we have shown that UBC4 expression occurs in a wide variety of rodent tissues. In contrast, in man, in particular in a normal individual, we have shown that there is a marked reduction in HUBC4 expression in brain tissue compared to other tissues suggesting that an aberration in HUBC4 expression is likely to be of most significance in brain tissue. This data correlates well with the neuronal lesions characteristic of the disease.

The invention will now be described, by way of example only, with reference to the accompanying Figures wherein;

BRIEF DESCRIPTION OF THE DRAWINGS

FIG. 1 shows the DNA sequence structure and the corresponding amino acid sequence structure of the HUBC4a genie found on human chromosome 14;

FIG. 2 shows the nucleotide and deduced amino acid sequence of HUBC4b cDNA. There is shown the nucleotide sequence and predicted amino acid sequence of the 3' region of the HUBC4b genie. The nucleotide sequence of the 3' end of an intron present within the HUBC4 is detailed in lower case letters. The 3' intron/exon junction splice site commutative intron branch point sequence are underlined;

FIG. 3 shows the partial cDNA sequence of mouse UBC4; and FIG. 4 shows the corresponding amino acid sequence structure of mouse UBC4;

The human chromosomal DNA used as a PCR substrate is indicated above each line (1-22, X, and Y). 'H' total human DNA positive control. 'Mo' mouse DNA negative control. 'Ha' Hamster DNA negative control. 'C' no DNA control. 'M' DNA markers (Φx 174 DNA/Hae III digested).

Figure 7A:
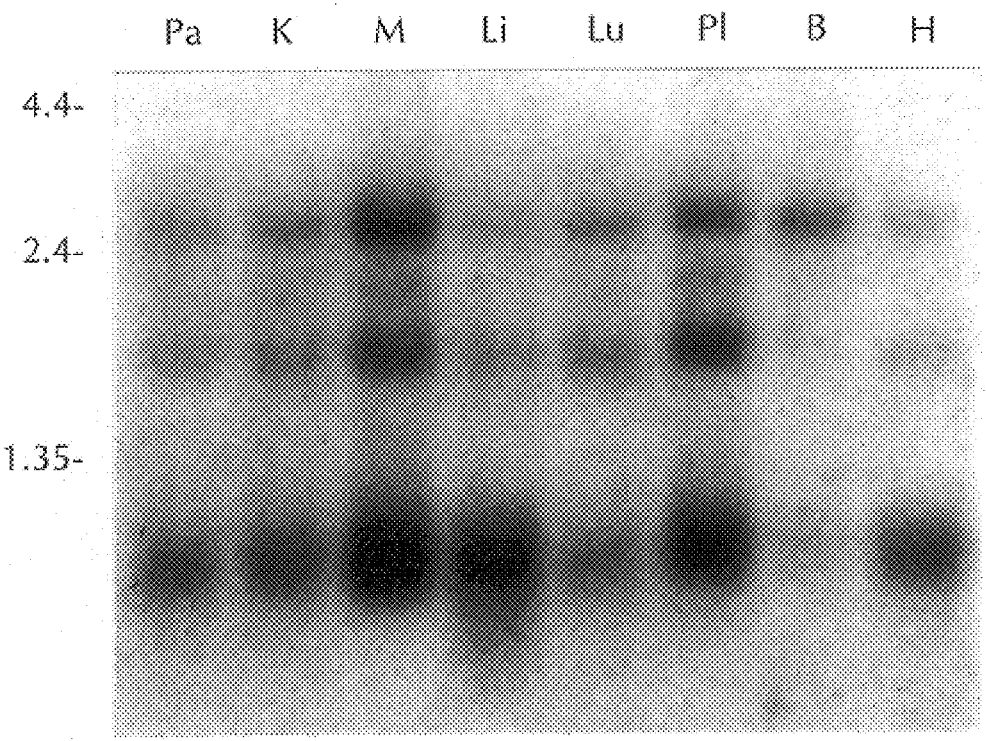
Figure 7B:
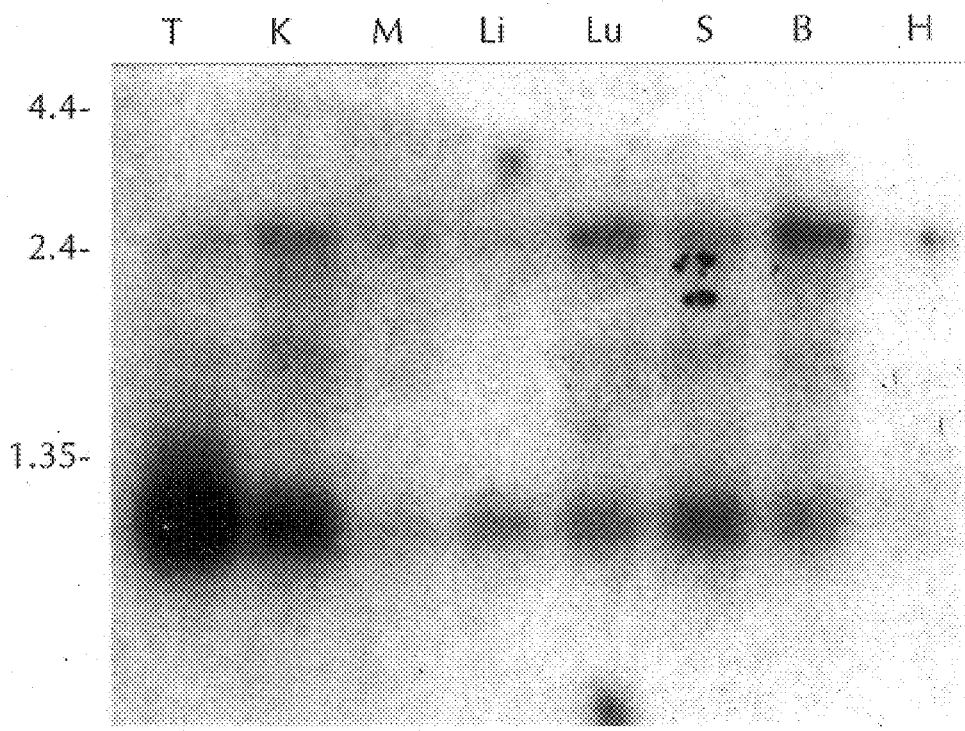
Figure 8:
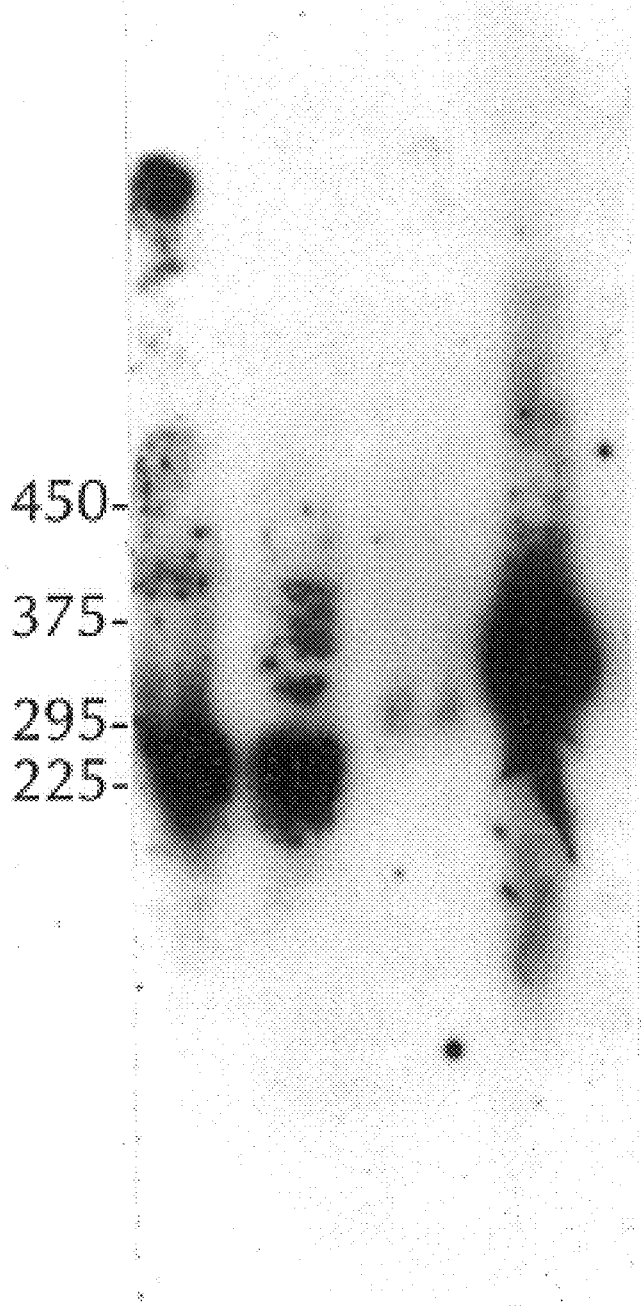
Figure 9A:
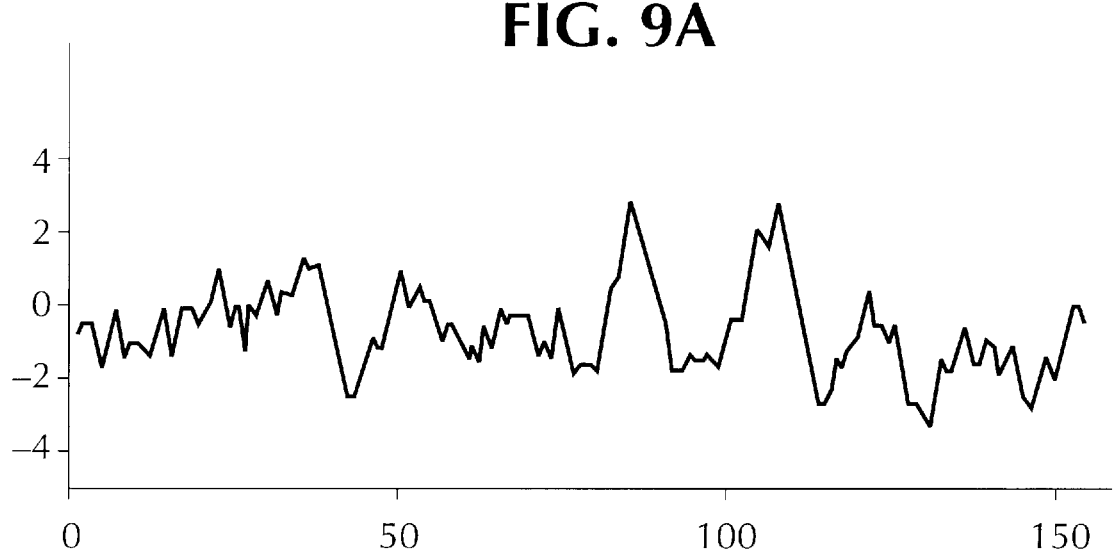
Figure 9B:
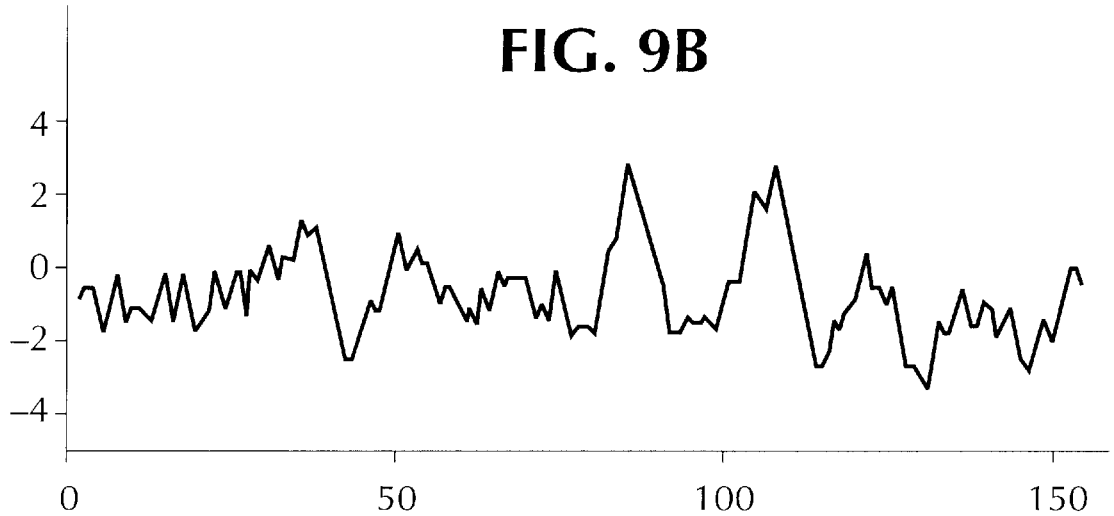
Figure 9C:
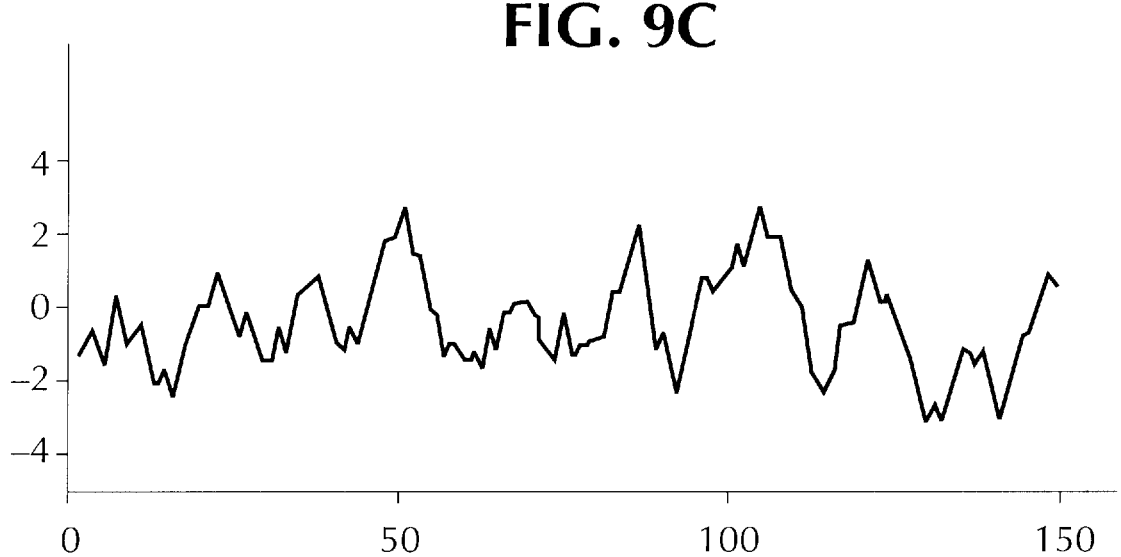

FIGS. 7A–7B shows a northern blot of mouse and human mRNA hybridised with an HUBC4a probe illustrating, tissue expression distribution;

FIG. 8 shows a pulsed field gel electrophoresis of the four YAC clones LMM-YAC1, 2, 3 and 4. The gel was Southern blotted and probed with an HUBC4b derived fragment as described hereinafter;

FIGS. 9A–9C shows a comparison of the hydrophobicity profiles of yeast UBC4 and human HUBC4a or HUBC4b to illustrate their similarity;

FIG. 10 shows a comparison of the primary amino acid sequence of HUBC4b with the primary amino acid sequences of a number of yeast, human and drosophilla ubiquitin conjugating enzymes and specifically UbcH2, UbcH5, UBC4, UbcD1, BEN and UbcD-2. The sequence data illustrates the similarity between the sequences and the predictable functional similarity between the corresponding proteins;

FIG. 11 shows alignment of predicted amino acid sequences encoded by the identified human (HUBC4a, HUBC4b, HUBC4c) and murine (mUBC4) genes. The full sequence of the protein encoded by HUBC4a is presented as the reference sequence. Identical residues encoded by HUBC4b, HUBC4c, and MUBC4, with respect to the reference sequence, are indicated with an asterisk (*).'-' represents shifting of the amino acid sequence to maintain alignment. '.' represents unknown amino acid composition;

FIG. 12 shows alignment of nucleotide sequences of the identified human HUBC4a gene, HUBC4b cDNA, HUBC4c gene, and the murine HUBC4 gene. The nucleotide sequence of HUBC4a is detailed as the reference sequence. Identical nucleotides encoded by HUBC4b, HUBC4c, and mUBC4, with respect to the reference sequence are indicated with an asterisk (*). '-' represents shifting of the nucleotide sequence maintain the alignment. '.' represents unknown nucleotides;

FIG. 13 shows primers used to amplify human and murine UBC4 genes. Primers (1), (3), (5), (7), (8), (9), and (11) were 5'-3' primers, and (2), (4), (6),(10) and (12) were 3'-5' primers with respect to the sequences detailed in FIGS. 1–3. Primer combinations. Primers (5), (6), (7), (8), (9) and (10) were used to specifically amplify human HUBC4 genes, or regions thereof, even in the presence of mUBC4. The PCR was performed using a preliminary denaturation step of 95° C. for 5 min, followed by cooling to 90° C., prior to adding Taq polymerase enzyme. Thirty-five cycles of the PCR were then performed at 62° C. for 15 sec, 72° C. for 20 sec, and 94° C. for 15 sec.

FIG. 14 shows nucleotide and predicted amino acid sequence of the charateristed region of the human gene encoding HUBC4c.

FIG. 15 shows variations in the HUBC4 genes and predicted amino acid sequences with respect to HUBC4a.

DETAILED DESCRIPTION OF THE PREFERRED EMBODIMENTS

The invention is concerned with the novel nucleotide sequences associated with the diseases described herein and presented in the Figures, especially FIG. 2. The gene of FIG. 2 encodes the novel protein HUBC4b. The corresponding cDNA clone is entitled LMM-cDNA1 and was deposited with the National Collection of Industrial and Marine Bacteria, 23 St Macher Drive, Aberdeen, AB2 1RY, Scotland on 10.5.94. Its deposition number is NC IMB 40626. The invention is also concerned with a novel mouse protein mUBC4. The corresponding cDNA clone is entitled LMM-cDNA2 and was deposited with the National Collection of Industrial and Marine Bacteria, 23 St Macher Drive, Aberdeen, AB2 1RY, Scotland on 10.5.94. Its deposition number is NC IMB 40637. The invention also concerns the whole genes described herein encoding the human cDNAs and their transcriptional control elements. Genes HUBC4a and HUBC4c are contained within the Yeast Artificial Chromosomes LMM-YAC1 (HUBC4a), LMM-YAC2, LMM-YAC3 and LMM-YAC4 (HUBC4c). These four YACs were also deposited with the National Collection of Industrial and Marine Bacteria, 23 St Macher Drive, Aberdeen, AB2 1RY, Scotland on 31.3.94. Their deposition numbers are respectively NC IMB 40627, NC IMB 40628, NC IMB 40629 and NC IMB 40630. The cosmids LMM-COS 1, LMM-COS2, LMM-COS3 were also desposited as above on 28.3.95 and their deposition numbers are 40711, 40712, 40713. They contain HUBC4b.

Isolation and Characterisation of HUBC4a, HUBC4b, HUBC4c, HUBC4d and HUBC4e (see FIGS. 1, 2 and 14)

The method will be described with particular reference to HUBC4b. HUBC4b clones were isolated during a differential hybridisation screen of normal oral palatal mucosa and octontogenic keratocyst cDNA libraries that had been prepared in lambda GEM2 bacteriophage vector. cDNA inserts of picked plaques were amplified by PCR using vector specific primers (T7 promoter primer and SP6 promoter primers)—30 cycles of 1 min 94° C., 2 min 50° C., 3 min 72° C.). These inserts were then purified by agarose gel electrophoresis.

Purified inserts were sequenced using the double stranded ds DNA cycle sequencing system (Life Technologies, Paisley, Scotland). In addition, inserts were radio-labelled using a random priming labelling kit manufactured by Boehriger Mannheim Ltd and [ -$^{32}$P]dCTP, and then used to screen Lambda ZAP cDNA library prepared from RNA extracted from normal oral palatal mucosa. Plaques giving a positive signal after high stringency washing were isolated, phagemids excised and sequenced using Sequenase Version 2.0 sequencing test (USB). cDNA sequence and deduced protein sequence is shown in FIG. 2a.

The method for isolation of the cosmids which encode the HUBC4b gene is as follows:

500,000 colony forming units (cfu) of a human cosmid genomic DNA library, prepared from human placental DNA in the vector pWE15 (Clontech, Cambridge Bioscience, Cambridge, UK), was screened with [$^{32}$P]-labelled HUBC4b cDNA probe. Positive clones were selected, plated at a lower density, and rescreened. A third round of screening was performed, if necessary, to isolate individual clones. Clones hybridising with the probe were cultured, and DNA was prepared according to standard methods. Cosmid DNA was restriction digested and subcloned into the pBluescript II vector (Stratagene Ltd, Cambridge, UK) for sequencing Isolisation and Characterisation of Mouse UBC4 (see FIGS. 3 and 4)

Human PCR primer pairs (1) and (4) as described below were used to amplify mouse mUBC4 directly from mouse genomic DNA. This DNA was then sequenced using a ds DNA cycle sequencing kit as described above. cDNA sequence and deduced protein sequence is indicated in FIG. 3 and FIG. 4. A high degree of homology was noted between the mouse and human sequences (compare FIGS. 1 and 2 with FIGS. 3 and 4).

Figure 5A:
FIGS. 5A–5C shows a fluorescent in situ hybridisation (FISH) demonstrating (a) chromosome localisation of HUBC4a to human chromosome 14q24.3 using the YAC LMM-YAC1. (b) Localisation of HUBC4c to human chromosome 12q using the YAC LMM-YAC4. (c) Localisation of HUBC4b to human chromosome 22q using the cosmid LMM-COS1.
Figure 5B:
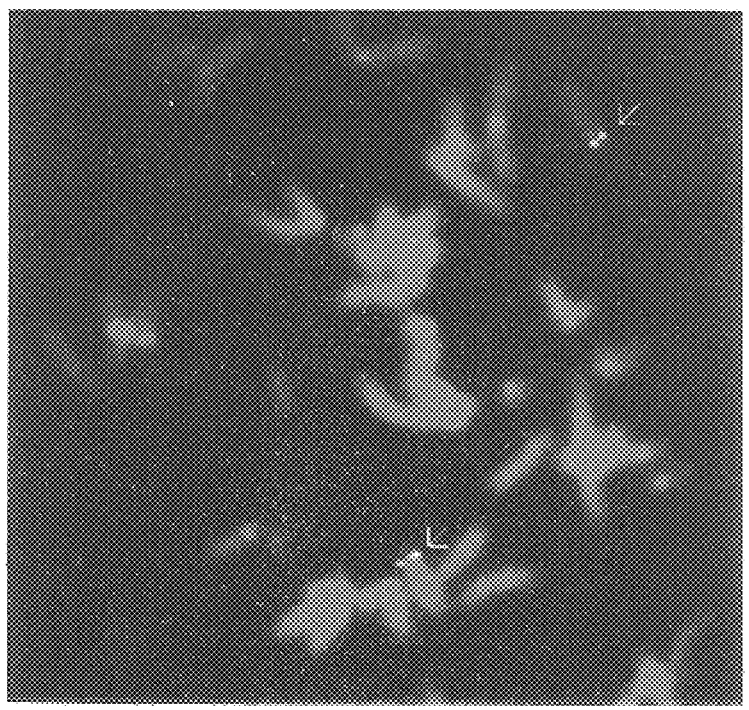
Figure 5C:
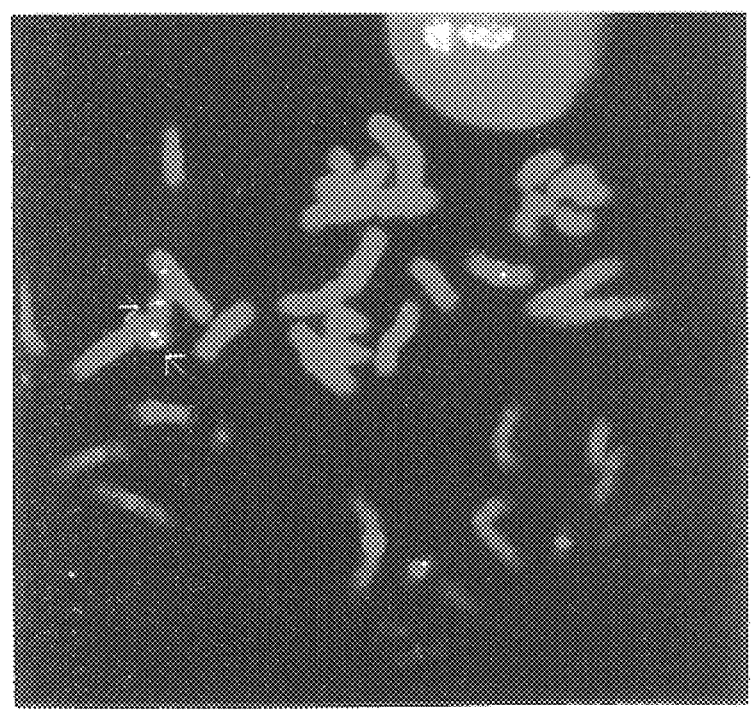
Figure 6A:
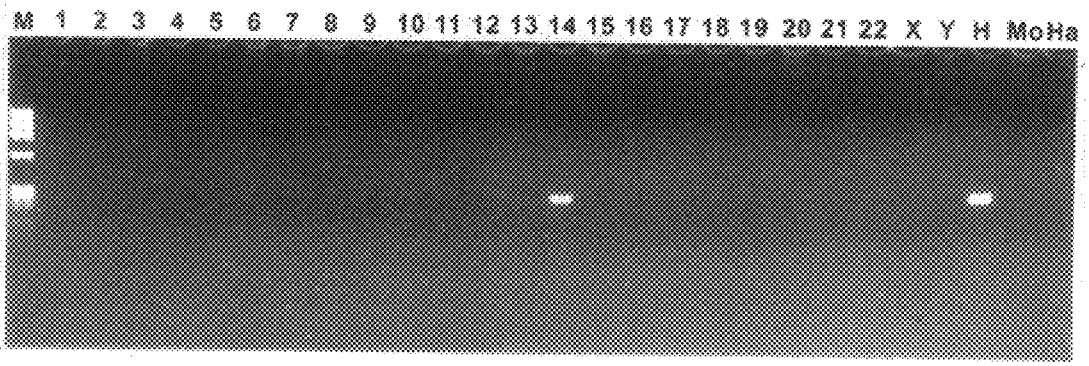
FIGS. 6A–6D shows chromosomal location of HUBC4a, HUBC4b, HUBC4c, HUBC4d and HUBC4e using the NIGMS iuman/rodent somatic cell hybrid mapping panel #2 version 2.
(a) Localisation of HUBC4a to human chromosome 14 with PCR primers
5'd=(GAAGCCAGCAACCAAACCCGA) and
5'd=(CACAAGCGAACGCCAGGC)
(b) Localisation of HUBC4b to human chromosome 22 using PCR primers
5'd=(TAGGAGGCAGCTTTGGCTT) and
5'd=(CACAAGCGAACGCCAGGC)
(c) Coamplification of HUBC4a and HUBC4b using PCR primers
5'd=(CCAGCCTGAGCACCCGCTT) and
5'd=(CACAAGCGAACGCCAGCC)
(d) Localisation of HUBC4a, HUBC4c, HUBC4d, and HUBC4e to human chromosome 14, 12, 19, and 13 respectively using PCR primers
5'd=(GAAGCCAGCAACCAAAACCGA) and
5'd=(GGTGTCTGAATGCACTGCA)
Figure 6B:
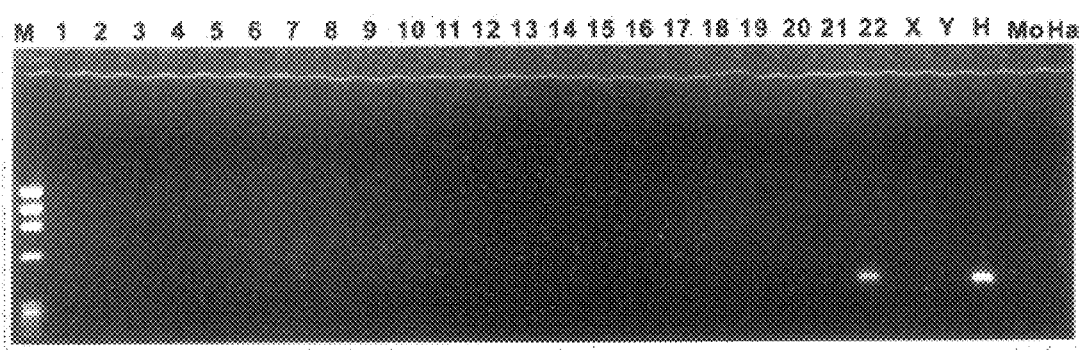
Figure 6C:
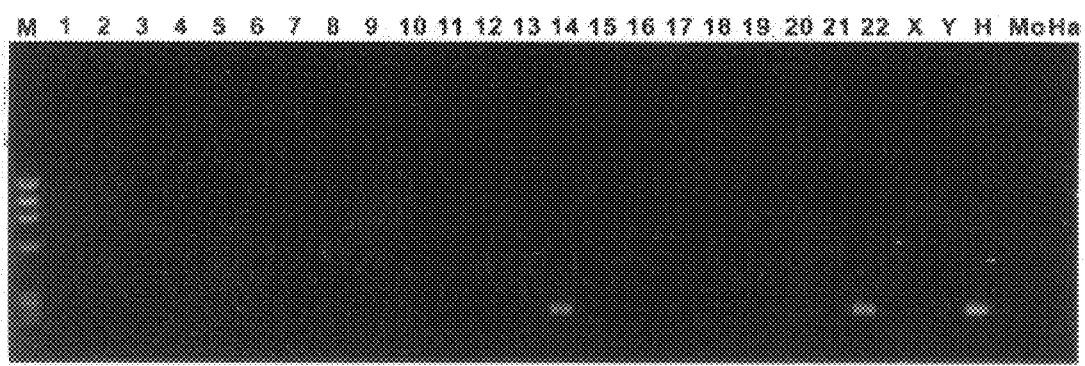
Figure 6D:
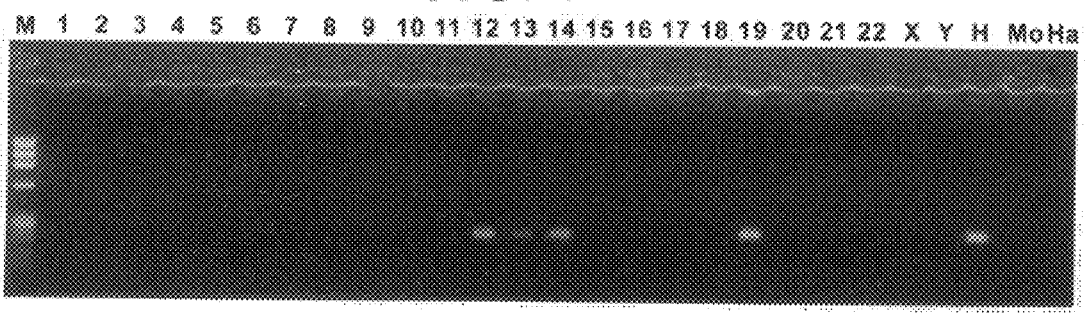

Chromosome Localisation of HUBC4 ie HUBC4a, HUBC4b, HUBC4c, HUBC4d, and HUBC4e (see FIGS. 5, 6 and 13)

PCR primers were designed for the amplification of human HUBC4 and mouse mUBC4 genes.
1. (5'-dGGCAGGTCTGTCTGCCAG)
2. (5'-dGGTCTCTGCTCACACTTGCTG)
3. (5'-dCAGCAAGTGTGAGCAGAGACC)
4. (5-dCTTTACAGGTTACCTAGACCAC)
5. (5-dGAAGCCAGCAACCAAAACCGA) and
6. (5-dCACAAGCGAACGCCAGGC).

Primers (1), (3) and (5) were 5–3' primers and (2), (4) and (6) were 3–5' primers with respect to the cDNA sequence. Primers (5) and (6) were used to specifically amplify human HUBC4a even in the presence of mouse mUBC40. Standard PCR conditions used a hot start after an initial 7 min incubation at 96° C., then cooling to 80° C. prior to the addition of polymerase enzyme followed by a 40 cycle PCR reaction of 45 sec at 94° C., 30 sec at 55° C. and 2 min at 72° C. Amplified products were analysed by agarose gel electrophoresis. Taq Polymerase and/or buffer was obtained from Promega Biotech. Deoxynucleotides were used at a final concentration of 200 μm and primers at 20 pmol/100 μl PCR reaction.

DNA extracted from NIGMS somatic cell hybrid panel no 2 (National Institute of General Medical Services USA obtained from the Coriell Cell Repository, 401 Haddon Avenue, Camden, N.J. 08103, USA) was used to chromosome localise HUBC4a. Primer pairs 5 and 6 were used for this purpose to avoid amplifying mouse mUBC4 from the mouse DNA present in somatic cell hybrids (see FIG. 6). Only one band of the same size as that of the human genomic DNA control was observed in the lane corresponding to chromosome 14 (see FIG. 6).

Fluorescence in situ hybridisation of metaphase spreads prepared using human chromosomes was preformed using biotinylated probes prepared by random priming of total HUBC4a YAC DNA from LMM-YAC1. A signal was obtained at a banding position on the chromosome corresponding to 14q24.3 (see FIG. 5).

Comparison of HUBC4a, HUBC4b and UBC4 (see FIGS. 9 and 10)

A comparison of HUBC4a and HUBC4b and UBC4 protein sequences is shown in FIG. 9. A 62% homology is found. A further comparison of the hydrophobicity profiles of human HUBC4b and yeast UBC4 protein sequences also demonstrated remarkably similar profiles (see FIG. 10). For example, the peaks and troughs at approximate amino acid positions 40, 70, 85, 100, 120 coincide in both proteins.

Comparison of Human and Mouse Expression Distribution of HUBC4b and MUBC4 using Northern Blots of RNA Extracted from Various Mouse and Human tissues (see FIG. 7)

Clontech multiple tissue Northern blots of RNA extracted from mouse and human (Cat Nos 7762-1 and 7760-1 respectively) were carried out as per manufacturer's instructions using a human HUBC4b DNA probe (prepared as described above). Bands corresponding to HUBC4b are indicated. The nature of the upper bands is not known. HUBC4 RNA transcripts were found in all tissues examined. Note the high levels of expression in mouse brain but the comparatively lower level in human brain (FIG. 7).

Isolation of Yeast Artificial Chromosomes Containing HUBC4 Sequences (see FIG. 8)

A Leeds University Molecular Medicine Unit YAC library prepared using human genomic DNA in the vector PYAC4 and in S cerevisiae strain AB1380 was configured for PCR screening in standard fashion. Primary DNA pools were screened with PCR primer pairs 11 and 12 (FIG. 13). Four positives were identified. Secondary and tertiary DNA pools were then screened to identify individual YAC's containing HUBC4 sequences. These YACs were then tested by PCR with the other HUBC4 primer pairs 3 and 4 and 5 and 6. Positive PCR signal patterns were obtained by analysis on agarose gel electrophoresis. No positive signal was observed with a control YAC. The four positive HUBC4-YACs (LMM 1-4) as judged from PCR were then subjected to pulse field gel electrophoresis. Southern blot analysis of these runs was performed by hybridising with a HUBC4b $^{32}$P-radio-labelled DNA probe, prepared as described above. Positive autoradiographic signals were achieved with all four YACs (see FIG. 8), LMM (1-4). Sizing of the human genomic DNA inserts in these separate YACs was performed by comparison of their positions of migration with those of the normal S cerevisiae chromosomes on ethidium bromide stained pulse field gels.

Preparation of Polyclonal Antisera

Peptide CKNAEEFTKKYGEKRPVD was conjugated to hemocyanin (keyhole limpet) using the heterobifunctional reagent MBS (m-maleimidobenzoyl-N-hydroxysuccinimide ester). Two rabbits (MAK-1 and MAK-2) were immunised with this conjugate. Rabbits were bled at regular intervals (3, 5, 7, 9 and 11 weeks) and antibody titre determined by ELISA (final titre approximately 1:1000). Antisera were collected after 11 weeks and antibodies affinity purified. The titres of the affinity purified antibody solutions were both approximately 1:3000.

Production of HUBC4 Gene Products by Baculovirus Expression

Expression of large quantities of protein encoded by the HUBC4b cDNA, and the HUBC4a gene was achieved using a baculovirus system.

Construction of Transfer Vector HUBC4b cDNA was PCR amplified from purified lambda GEM-2 bacteriophage cDNA clones using vector specific primers (T7 promoter primer and SP6 promoter primer). The cDNA was digested from the flanking vector sequence by restriction digestion using Xba I and Eco RI. The insert was gel purified and ligated into the similarly digested transfer vector pBacPAK9 (Clontech). The ligation mixture was transformed into competent E. coli DH5α cells, and recombinants were sequenced to confirm the integrity of the cloned cDNA.

DNA encoding the HUBC4a open reading frame region was generated as described in 'production of vectors encoding antisense HUBC4 genes'. The PCR product was blunt ended using T4 DNA polymerase, and it was then cloned into the Sma 1 site of pBacPAK9. Recombinants were selected containing inserts in the correct orientation for transcription of the open reading frame.

Preparation of Linearised Viral DNA

Bsu 361 linearised BacPAK6 DNA was obtained from Clontech, or produced from circular viral DNA by restriction digestion with Bsu 361 essentially as described by Kitts and Possee (993). 2 µm of virus DNA was digested overnight at 37° C. with Bsu 361 in restriction enzyme buffer, and then heat inactivated by incubation at 65° C. for 10 min. The DNA was then stored at 4° C.

Cotransfection of Viral DNA and Recombinant Transfer Vector

Cotransfection was performed according to the procedure of King and Possee (1992). 35 mm petri dishes were seeded with $1.5 \times 10^6$ Spodoptera frugiperda cells and then incubated at 28° C. for 2 b. 2.5 µg of recombinant transfer vector DNA and 0.5 µg of linearised viral DNA were mixed in a sterile 5 ml glass bijou in a volume of 25 µl. 2.5 µl of lipofectin (diluted 2:1 with sterile water) (Gibco-BRL) was added to the DNA and the mixture incubated for 15 min at room temperature. Immediately prior to transfection, the cell monolayers were washed with 2 ml of serum-free TC100 medium whereafter the monolayer was covered with 1.5 ml of medium to which the DNA/lipofectin mixture was added. The plates were incubated at 28° C. for 8 h and the medium was then replaced with TC100 medium supplemented with 10% (v/v) foetal calf serum. The dishes were incubated for a further 2 days whereafter the supernatant was harvested for virus purification.

Virus Purification 35 mm petri dishes were seeded with $1.5 \times 10^6$ Spodoptera frugiperda cells and then incubated at 28° C. for 2 h. Thne medium was removed, and 0.1 ml of diluted virus suspension ($10^0$, $10^1$, $10^2$, $10^{-3}$, and $10^{-4}$ dilutions) was gently pipetted into the centre of each dish. Virus was allowed to adsorb for 1 h at room temperature, after which the inoculum was removed and the cell layer covered with 2 ml of 37 overlay [1% (w/v) low gelling temperature agarose, 50% (v/v) TC100 medium, and 2.5% (v/v) foetal calf serum]. After the overlay had solidified, 1 ml of TC100/2.5% foetal calf serum was added to supplement the medium, and the plates were incubated for 3 days at 28° C. in a humidified atmosphere. Recombinant virus plaques were identified by staining with X-gal, in the presence of neutral red. Putative recombinant plaques were identified as white plaques. Positive plaques were picked into 0.5 ml of TC100/foetal calf serum and retitrated. Two rounds of plaque purification were performed to generate pure stocks of recombinant virus.

Isolation of HUBC4 Gene Products

For the production of large amounts of expressed HUBC4 gene products Spodoptera frugiperda cells were grown to a density of approximately $10^6$/ml in 21 spinner flasks containing 50 ml of TC100/2.5% fetal calf serum. Cells were infected at a multiplicity of infection of 3–5, and then incubated at 28° C. for 3 days. To recover the protein, cells were pelleted from the medium by centrifugation at 5000 g for 10 min. The cells were then washed in phosphate buffered saline and then lysed by sonication in the presence of TENT buffer [100 mM Tris-Cl, pH7.5, 0.1M NaCl, 1% (v/v) Triton X-100, 1 mM EDTA] containing 1 mM NEM and 1 mM PMSF. The released protein was precipitated Using ammonium sulphate then purified by FPLC.

REFERENCES

King, L. A. and Possee, R. D. (1992). "The bacuolvirus expression system, a laboratory guide", pp 1–229. Chapman and Hall, London.

Kitts, P. A. and Possess, R. D. (1993). A method for producing recombinant virus expression vectors at high frequency. Biotechniques 14, 810–817.

Production of Vectors Enconding Antisense HUBC4 genes

Construction of HUBC4 Anti-Sense RNA Expression Vectors

HUBC4b cDNA was PCR amplified from purified lambda GEM2 bacteriophage HUBC4b cDNA clones using vector specific primers (T7 promoter primer and SP6 promoter primer). The cDNA was digested from the flanking vector sequence by restriction digestion with Xba I and Eco RI. The insert was cloned into Xba I IEco RI digested prokaryotic/ eukaryotic expression vector pBK-CMV (Stratagene). Plasmids were transformed into competent E. coli XLI-Blue MRF, selecting colonies containing inserts for sequence analysis to confirm correct insert orientation and sequence integrity. Transcription from the CMV immediate early promoter of the anti-sense HUBC4b construct (pLMM-AS1) results in transcription of the anti-sense strand of the HUBC4b cDNA.

For HUBC4a anti-sense expression vector construction, the gene was first PCR amplified from human genomic DNA using oligodeoxynucleotide primers (5'-dATGGCGGCCAGCAGGAGGCTG 3' and 5'd-CTTTACAGGTTACCTAGACCAC 3'). The PCR product was blunt ended using T4 DNA polymerase, and ligated into the Sma I site of the pBK-CMV vector. Ligation products were transfromed into E. coli XLI-Blue MRF. Colonies containing cloned insets were sequenced, selecting those containing the insert in the anti-sense orientation (designated pLMM-AS2).

Cell Culture

HeLa cells were maintained in DMEM supplemented with 10% fetal calf serum, 10 µg/ml steptomycin, and 50 µg/ml penicillin. To construct anti-sense cell lines, cells were transfected with pLMM-AS1 or pLMM-AS2 using the cationic-liposome DOTAP as detailed in 'liposome-mediated delivery of nucleic acids and proteins to eukaryotic cells'. Selection for maintenance of the vector was achieved by inclusion of the drug G418 in the cell culture medium.

Liposome Mediated Delivery of Nucleic Acids and Proteins to Eukaryotic Cells

Transfection of cells with nucleic acids containing sequence encoding gene(s), cDNA(s), oligonticleotides containing sequence complementary to HUBC4/mUBC4, or parts thereof, or of proteins encoded by HUBC4/mUBC4 genes, or parts thereof, was achieved using DOTAP, N-[1-2,3-Diolcoyloxy)propyl]-N,N,N-trimethyl ammonium methylsulphate (Boehringer Mannheim), a cationic-liposome transfection reagent.

Method for Transfection of Cells

Cell Preparation $1-3 \times 10^5$ aliquots of adherent tissue culture cells were passaged into 60 mm diameter tissue culture dishes containing 5–6 ml of tissue culture medium the day prior to transfection.

Preparation of Nucleic Acid/Liposome Complex

5 µg of DNA was diluted to 0.1 µg/ml in HEPES buffer [20 mM HEPES(cell culture grade), pH7.4] in a sterile reaction tube. In a second tube, 30 µl DOTAP was diluted to 100 μl in HEPES buffer. The 50 μl nucleic acid solution was mixed with the DOTAP suspension, gently mixed by pippeting, and then incubated for 15 min at room temperature.

Cell Transfection

Immediately prior to transfection, the DOTAP/nucleic acid mixture was mixed with 5–6 ml of sterile tissue culture medium. The medium covering the cells was poured off, and the DOTAP/nucleic acid containing medium was added to the cells. The cells were incubated at 37° C. for 6 hours whereafter the medium was replaced with fresh culture medium.

Expression of HUBC4 in Prokaryotic Cells

Blunted ended HUBC4 insert (10 ng) was generated by both RT-PCR (reverse transcribed polyerase chain reaction) and also PCR of genomic DNA and sub-cloned into the Sma 1 restriction endonuclease site of pGEX-3X (100 ng). This DNA construct was then used to transform competent E. coli DH5α cells (100 μl). Transformed cells were selected by growth on LB agar plates containing 50 μg/ml ampicillin.

Plasmid DNA was isolated from an overnight culture of selected colonies and sequenced to establish the presence of insert in the correct reading frame for expression of glutathione S-transferase fusion protein product.

A 1:100 dilution of overnight culture of transformed cells containing insert was grown to optical density of 0.5 (at wavelength 600 nm). Isopropyl-β-D-thiogalacloside was then added to a concentration of 1 mM and the cells grown for an extra 5 hr.

Cell extracts were prepared as follows. Broth was centrifuged (2000 g for 10 min) and cell pellet collected. These cells were then resuspended in PBS (140 mM sodium chloride, 2.7 mM potassium chloride, 10 mM disodium orthophosphate and 1.8 mM potassium dihydrogen phosphate pH 7.3). Cells were sonicated and Triton X100 added to a final concentration of 1% and mixed for 30 min. Extract was then centrifuged. Supernatant was used for the affinity purification of fusion protein.

Supernatant was mixed with glutathione-Sepharose 4B equilibrated with PBS containing 1% Trion for 30 min. This suspension was then sedimented by centrifugation at 500 g for 5 min. The Sepharose pellet was washed with PBS three times. Fusion protein was then eluted by incubation of the Sepharose beads for 10 min at 20° C. with 50MM tris/HCI buffer, pH 8.0, containing 10 mM glutathione. This elution procedure was repeated a further two times.

Production of Transgenic Animals by Microinjection

DNA microinjection and transgenic animal production were carried out essentially as described in Chapter 2 of Transgenic animal technology; A laboratory handbook. Edited by Carl A. Pinkert; Academic Press Inc. 1994. Briefly, this involved:

1. Super ovulation of 6 week old female F1 hybrid mice (CBA/J×C57B1/6) by intraperitoneal injection of 5 units of pregnant mare's serum gonadotrophin (PMSG) followed 47 hours later by 5 units of human chorionic gonadotrophin (HCG).

2. Super ovulated donor dams were caged with fertile male mice following injection with HCG. The following morning, females were checked for copulatory plugs, the presence of which was taken as a sign of mating.

3. Mated females were sacrificed using a schedule 1 method and the oviducts removed. Eggs were released from the oviduct into hyaluronidase M2 medium by tearing with forceps. After washing with M2 medium, eggs were incubated at 37° C., 5% $CO_2$ in M16 medium prior to DNA microinjection.

4. Plasmid DNA constructs fro microinjection were prepared using standard cloning techniques and purified to a high decree by isolating supercoiled DNA from caesium chloride gradients (performed twice). Plasmid constructs were linearised to remove vector sequences prior to purification using phenol/chloroform ethanol precipitation. YAC DNA was prepared for injection according to the method of Schedl et al., 1993, Nature 362, 258–261.

5. DNA at a concentration of 2–4 ng/μl was injected into fertilised oocytes using a specialised microscope (Zeiss) fitted with micromanipulators (Narashige). Needle preparation for holding and injection pipettes was performed using a Sutter model P-87 pipette puller following the method described in Pinkern 1994.

6. Injected oocytes were transferred into the oviduct of pseudopregnant recipient dams made pseudopregnant by mating with vasectomised males. Recipient dams were placed under general anaesthetic and a 5mm surgical incision made above the ovarian fat pad. The fat pad along the ovary and oviduct were exteriorised and held in position with a serafin clip. The bursa surrounding the ovary was torn with forceps to reveal the infundibulum. Using a glass capillary needle injected oocytes (15–20) were blown into the infundibulum using mouth pipetting and with the aid of a stereo dissecting microscope. The reproductive tract was carefully replaced in the abdomen and the body wall and skin closed with sutures.

7. Recipient dams were allowed to recover and to give birth. Weaned offspring were analysed for the presence of the transgene by Southern blotting or PCR analysis of genomic tail DNA.

Production or Transgenic Animals Using Homologous Recombination in Embryonic Stem (ES) Cells Introduction of mutations into HUBC4 and HUBC4 genes and generation of null mutations was achieved using homologous recombination in ES cells. Targeting vectors were constructed using standard cloning procedures. A replacement type vector (Deng et al., 1993; Mol. Cell. Biol. 13(4), 2134–2140) was used to substitute the coding region of the gene with the neo$^r$gene thus conferring neomycin resistance on targeted cells. A negative selection marker, the herpes simplex virus thymidine kinase (HSV TK) was included at the 3' end of the targeting construct to select against random integration events. To introduce mutations into the UBC coding and flanking sequences insertion type vectors were also made (Deng et al. 1993, as above). In addition gene targeting and production of conditional targeted mutants using the CreloxP recombination system of bacteriophage P1 as described by Gu et al., 1993. Cells 73, 1155–1164 was employed. The different types of targeting construct were introduced into ES cells and used to produce transgenic mice by the same method as described in Gene Targeting—A Practical Approach Edited by A. L. Joyner IRL Press Oxford 1993. Briefly, this involves:

1. Culture of ES cells (mouse strain 129 derived) on mitotically arrested neo$^r$ feeder layers of primary mouse embryonic fibroblasts in DMEM+20% foetal calf serum at 37° C.

2. Transfection of targeting constructs into ES cells by electroporation in a Biorad gene pluser at 500 μF, 240 v for 6 msec. Allow cells to recover and seed petri dishes containing mitotically arrested feeder layers with the ES cells. After 24 hours, positive selection is started by the addition of 350–400 μm/ml of G418 and negative selection with either 2 μm gancycolvir or 0.2 μm FIAU. The medium is replaced daily and resistant colonies identified after 9–11 days.

3. Surviving ES cell colonies were screened individually for homologous recombination at the targeted locus using PCR and confirmed using Southern blotting using genomic DNA from the ES cells.

4. Targeted ES cells clones were expanded and aliquots frozen prior to injection into blastocysts. Cells were prepared for injection by washing twice with PBS, followed by trypsinisation of the cells from the culture dish. The ES cells were dissociated in culture medium by repeated pipetting and the cell suspension transferred to a culture dish and incubated at 37° C. for 1 hour to allow the ES cells to separate from the feeder layer. After removing the supernatant, ES cells were detached from the culture dish by repeated pipetting with culture medium, pelleted by centrifucation and then resuspended in 100–500 μl culture medium prior to blastocyst injection.

5. C57B 1/6 blastocysts were flushed from the uteri of mated females at 3.5 days post coitum and incubated in M 16 medium at 37° until used for injection.

6. Blastocysts were injected with ES cells using an inverted microscope (Zeiss) and specialised micromaniptilators (Narashige) designed for production of transgenic animal. 10–15 ES cells were injected into each blastocyst and the injected blastocysts incubated in M16 medium for 1–2 hours prior to implantation in pseudopregnant foster mothers.

7. Injected blastocysts were implanted into the uterus of 2.5 day post coitum pseudopregnant females made by mating normal females with vasectomised males. Resulting male chimeric offspring (as determined by coat colour) were mated with C57VL/6 females to test for germline transmission of the transgene. The offspring of germline chimeras were used to establish a breeding colony and produce experimental animals on different genetic backgrounds.

Diagnosis of Alzheimer's Disease

Using the DNA and protein sequence structure disclosed in FIGS. 1, 2 or 14 polynucleotide probes (see FIG. 13 for examples) for diagnostic purposes may, if desired, be constructed which are capable of hybridisation to any portion of the DNA protein or RNA sequence regardless of whether the portion is capable of translation into a polypeptide or not. Moreover, if desired the protein HUBC4 in the form of an RNA sequence may be transcribed into a corresponding cDNA sequence using, for example, reverse transcriptase and the protein determined by the use of a polynucleotide probe capable of hybridising to any portion of the cDNA sequence. It will be appreciated that the polynucleotide probe will comprise a nucleotide sequence capable of hybridisation to a sufficient length of the sequence to be determined, to ensure that the probe will be capable of hybridisation to at least eight consecutive nucleotides of the sequence to be determined, preferably to at least 10 consecutive nucleotides, more preferably to at least 12 consecutive nucleotides and especially to at least 14 consecutive nucleotides. The polynucleotide process of the present invention may be labelled or marked according to techniques known in the art, for example, $^{32}$P radio-labelled in any conventional way, or alternatively radio-labelled by other means well known in the hybridisation art, for example, to give $^{35}$S radio-labelled probes. The probes may if desired carry fluorescent markers. They may alternatively be labelled with Biotin or similar species by the method of D C Ward et al as described in proceedings of the 1981 ICN/UCLA Symposium on Development Biology Using Purified Genes held in Keystone, Colo. on Mar. 15–20 1981, volume xxiii, 19891, pp647–658, Academic Press; editor Donald E Brown et al, or even enzyme labelled by the method of A D B Malcolm et al, Abstracts of the 604th Biochemical Society Meeting, Cambridge, En-land (meeting of Jul. 1 1983). The aforementioned protein HUBC4 may also be determined by the use of antibodies which may be polyclonal but are preferably monoclonal, raised to a polypeptide sequence coded for by at least a portion of the aforementioned genomic DNA sequence or corresponding RNA sequence. The antibody may thus bind to the protein encoded by the aforementioned genomic DNA sequence or corresponding RNA sequence or bind to any fragment of the protein. In addition, antibody fragments, as aforedescribed, may also be used for this purpose.

The said antibodies of the present invention may, if desired, carry a label or marker component, for example, as hereinbefore described in relation to the polynucleotide probes of the present invention. Thus the antibodies may, for example, carry a fluorescent marker. It is not, however, necessary that the antibodies of the present invention carry a label or marker component. Thus, for example, the antibodies of the present invention may be identified by a second antibody which is an antibody to antibodies of the present invention, for example, goat anti-mouse immunoglobulin. In this instance, the second antibody will have a labelled or marker component.

For the diagnosis of a predisposition to Alzheimer's Disease, the invention may be conveniently practised in the following fashion. mRNA is isolated from the peripheral white blood cells of the subject for investigation by standard techniques. This is copied into single stranded cDNA using oligo-dT as a primer and, for example, reverse transcriptase. The single stranded cDNA may be converted into a double stranded form arid cloned in a plasmid. bacteriophage or cosmid vector. Clones containing the HUBC4 sequences may be identified using polynucleotide probes from within the HUBC4 gene sequence as defined above. The cDNA sequence in such clones may be determined using standard techniques, for example, using an Applied Biosystems Model 373A-01 DNA Sequencer. The sequence thus obtained can be compared with the normal sequence provided for HUBC4 herein. In this way any mutations occurring in the HUBC4 mRNA in the individual under investigation will be detected. It will be appreciated by the skilled man that alternative methods of analysis of mRNA in patient samples can be used in the practice of the invention. For example, the technique of RT-PCR (Reverse Transcription Polymerase Chain Reaction) may be applied. In this case, one of both of the oliogonucleotides used in a PCR reaction will be derived from within the HUBC4 coding sequences provided herein (see FIG. 13).

An alternative method of putting the invention into practice would involve the analysis of DNA from an individual. Such analysis is conveniently performed by PCR amplification of the HUBC4 genes using polynucleotides or oligonucleotides capable of hybridising to any portion of the HUBC4 cDNAs or to any portion of the HUBC4 genes or to any portion of the DNA sequence contained within the Yeast Artificial Chromosomes LMM-YAC1, LMM-YAC2, LMM-YAC3 or LMM-YAC4 or the cosmids LMM-COS1, LMM-COS2 and LMM-COS3. PCR products thus obtained may be conveniently sequenced directly by methods well known in the art to establish differences between sequences in an individual and the normal sequence of the HUBC4 genes.

The practice of the invention can further be carried out by the insertion of HUBC4 cDNA or gene sequences into a gene targeting vector designed to allow homologous recombination between exogenous targeting DNA and endogenous target gene, for example, in mouse embryo stem cells in culture. Homologous recombination may be performed using variants of the human or mouse UBC4 gene with either the normal or specific mutant sequences. The technique of gene knockout may be employed by performing homologous recombination between the UBC gene in mouse or other animal species and in particular in embryonic stem cells derived therefrom, with a modified UBC4 gene of the type disclosed herein where the coding sequence of such UBC4 gene has been deliberately disrupted by the insertion of exogenous nucleic acid sequence. Such exogenous nucleic acid sequence may, for example, be itself capable of encoding a protein. For example, a gene encoding a protein confirming neomycin resistance can be inserted into UBC4 coding sequences so that after homologous recombination UBC function is destroyed whilst the transfected cell line becomes capable of growth in large quantities of neomycin or G418. A variety of other techniques well known in the art for production of transgenic animals are equally applicable in the practice of the present invention. This will include the direct injection of UBC4 nucleic acid sequences into pronuclei or to introducing such mutations by transfection of embryonic stem cells, reintroduction into blastocysts and the breeding of chimeric animals.

The method of the invention may also be performed by the use of antibodies recognising epitopes within the HUBC4 proteins derived as discussed above. Individuals who have HUBC4 alleles which result in the generation of a truncated form of the protein may be identified by Western blot analysis of proteins from, for example, their peripheral blood white cells or in cells obtained by lumbar puncture from the cerebrospinal fluid. Heterozygotes for HUBC4 mutations (and individuals who are hence at risk of AD given that the disease is autosomal dominant) will display proteins of two sizes when analysed by Western blots with the antibodies of the present invention. Such individuals will produce a normal protein plus a shorter truncated version. In a similar fashion it will be possible to detect splice variants of the HUBC4 protein which may in fact produce variant HUBC4s which are larger than normal.

Treatment of a Degenerative Disease

The DNA and/or protein sequence stricture, or any part thereof shown in FIGS. 1, 2 or 14 can be used for the treatment of the disease insofar as non-mutant versions of HUBC4 can be manufactured using conventional techniques and subsequently delivered, again using conventional delivery means (see section above "Liposome mediated delivery of nucleic acids and proteins to eukaryotic cells), to a target site with a view to preventing the onset of a degenerative disease such as Alzheimer's Disease, or alternatively, mitigating the effects of a degenerative disease such as Alzheimer's Disease or Down's Syndrome.

The DNA sequence structure shown in FIGS. 1, 2 14, or any part thereof may be recombinantly introduced into a host cell (see section above "Expression of HUBC4 in prokaryotic cells") and subsequently expressed for the purpose of supplying the corresponding protein. This protein may be packaged within a liposome and delivered to the CNS directly by injection or the like.

Alternatively, conventional recombinant vectors may be used to carry the genetic sequence structure, or part thereof, shown in FIGS. 1, 2 or 14 to the target site and also to express said sequence structure so as to provide a non-mutant form of ubiquitin conjugating enzyme at the target site.

The Development of Therapeutics

Using conventional techniques non-human transgenic animals can be produced, which animals would be provided with mutant forms of the genes and corresponding proteins shown in FIGS. 1, 2, 3, 4 and 14. In addition, these animals may be modified such that these genes, or a part, are absent or not expressed. Such animals will have a predisposition towards a degenerative disease such as Alzheimer's Disease or cancer and will be useful in subsequent investigations for the development and testing of therapeutic agents active against a degenerative disease such as Alzheimer's Disease or cancer.

REFERENCES

1. Proc. Natl. Acad. Sci. USA Vol 91 pp 8797–8801 (1994) Identification of a human ubiquitin-conjugating enzyme that mediates the E6-AP-dependent ubiquitination of p53.
2. Journal of Biological Chemistry Vol 269 No. 13 pp 9582–9589 (1994) Degradation of the Tumour Suppressor Protein p53 by the Ubiquitin-mediated Proteolytic System Requires a Novel Species of Ubiquitin-Carrier Protein, E2.
3. Cell Vol 75, 495–505 (November 1993) The HPV-16 E6 and E6-AP Complex Functions as a Ubiquitin-Protein Ligase in the Ubiquitination of p53.
4. Journal of Biological Chemistry Vol 269 No. 13 pp 9574–9581 (1994) Purification and Characterisation of a Novel Species of Ubiquitin-Carrier Protein E2, That Is Involved in Degradation of Non-"N-end Rule" Protein Substrates.
5. Proc. Natl. Acad. Sci. USA Vol. 90 pp 10484–10488.
6. J. Biolog Chem Vol. 269 pp 8797–8802.
7. Genomics 12 447–453.
8. Rogers S. et al Science 234 364–368 1986.

We claim:

1. An isolated nucleic acid molecule which encodes a polypeptide, said polypeptide having an amino acid sequence encoded by a nucleic acid molecule having a nucleotide sequence selected from the group consisting of SEQ ID NO: 1, 3, 4, 6 and 8.

2. The isolated nucleic acid molecule according to claim 1 wherein said isolated nucleic acid molecule is from a human.

3. The isolated nucleic acid molecule according to claim 1 wherein said isolated nucleic acid molecule is from a mouse.

4. The isolated nucleic acid molecule according to claim 1 wherein said nucleic acid molecule has a nucleotide sequence selected from the group consisting of SEQ ID NOS: 1, 3, 4, 6 and 8.

5. The isolated nucleic acid molecule according to claim 1 wherein SEQ ID NO: 1 comprises N at residue position 320, wherein N is V.

6. The isolated nucleic acid molecule according to claim 1 wherein SEQ ID NO: 1 comprises N at residue position 605, wherein N is B.

7. The isolated nucleic acid molecule having a nucleotide sequence which is fully complementary to a nucleotide sequence selected from the group consisting of SEQ ID NO: 1, 3, 4, 6 and 8.

8. The isolated nucleic acid molecule according to claim 7 further comprising a label.

9. An isolated nucleic acid molecule, which hybridizes in Taq polymerase buffer at 65° C. to a nucleic acid molecule having a nucleotide sequence set forth in SEQ ID NO: 1 or 8, and wherein said isolated nucleic acid molecule has a complementary sequence that hybridizes in Taq polymerase buffer at 65° C. to a nucleic acid molecule having a nucleotide sequence selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

10. The isolated nucleic acid molecule according to claim 9 further comprising a label.

11. An expression vector comprising an isolated nucleic acid molecule according to claim 1, operatively linked to a promoter.

12. The expression vector according to claim 11 further comprising an enhancer.

13. The expression vector according to claim 11 wherein the isolated nucleic acid molecule comprises a nucleotide sequence selected from the group consisting of SEQ ID NOS: 1, 3, 4, 6 or 8.

14. An isolated cell line or strain transformed with an expression vector according to claim 11.

15. A process for producing a recombinant cell which produces a polypeptide encoded by the isolated nucleic acid molecule according to claim 1, wherein said process comprises transfecting a cell with said isolated nucleic acid molecule and isolating said recombinant cell.

16. The process according to claim 15 wherein said cell has the capacity to export said polypeptide.

17. The process according to claim 15 wherein said cell is transfected with a mixture comprising a liposome transfection reagent and said isolated nucleic acid molecule.

* * * * *

UNITED STATES PATENT AND TRADEMARK OFFICE
CERTIFICATE OF CORRECTION

PATENT NO. : 5,952,481
DATED : September 14, 1999
INVENTOR(S) : Markham et al.

It is certified that error appears in the above-identified patent and that said Letters Patent is hereby corrected as shown below:

Column 1,
Line 39, change "suicIh" to read as -- such --.
Line 47, change "vet" to read as -- yet --.

Column 3,
Line 1, change "multiujbiquinated" to read as -- multiubiquinated --.

Column 7,
Line 12, change "tip" to read as -- up --.

Column 10,
Line 19, change "stricture" to read as -- structure --.
Line 25, change "stricture" to read as -- structure --.

Column 12,
Line 63, change "FIGS. 1 or 14" to read as -- FIGS. 1, 2 or 14 --.

Column 14,
Line 18, change "stricture" to read as -- structure --.
Line 23, change "analogies" to read as -- analogues --.
Line 50, change "genie" to read as -- gene --.

Column 15,
Line 26, change "DNA/HaeI11" to read as -- DNA/Hae III --.

Column 16,
Line 9, change "characteristed" to read as -- characterised --.

Column 17,
Line 12, insert a period after "sequencing" to read as -- sequencing. --.
Line 23, change "ie" to read as -- i.e. --.

Column 18,
Line 58, start a new paragraph after the heading "Construction of Trasnfer Vector".

UNITED STATES PATENT AND TRADEMARK OFFICE
CERTIFICATE OF CORRECTION

PATENT NO. : 5,952,481
DATED : September 14, 1999
INVENTOR(S) : Markham et al.

It is certified that error appears in the above-identified patent and that said Letters Patent is hereby corrected as shown below:

Column 19,
Line 12, change "(993)" to read as -- (1993) --.
Line 21, change "2b." to read as -- 2h. --.
Line 37, change "Thne" to read as -- The --.

Column 20,
Line 50, change "oligonticleotides" to read as -- oligonucleotides --.

Column 22,
Line 1, change "fro" to read as -- for --.
Line 3, change "decree" to read as -- degree --.
Line 15, change "pinkern" to read as -- pinkert --.
Line 36, change "HUBC4" to read as -- mUBC4 --.
Line 64, change "6msec" to read as -- 6msec --.

Column 23,
Line 27, change "animal" to read as -- animals --.

Column 24,
Line 9, change "En-land" to read as -- England --.
Line 10, change "Ju. 1" to read as -- 1 July --.
Line 39, change "arid" to read as -- and --.

Column 25,
Line 50, change "stricture" to read as -- structure --.

Signed and Sealed this

Twentieth Day of November, 2001

Attest:

NICHOLAS P. GODICI
Attesting Officer  Acting Director of the United States Patent and Trademark Office

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
        (A) LENGTH: 1000 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 1:

| | | | | | |
|---|---|---|---|---|---|
| CCAGCCTCGC | CAATATGGTG | AAACCCGTTT | CTACTAAAAA | TATTTAAAAA | ATTAGCCAGG | 60
| CGTGGTGGCA | ATCACCTGTA | ATCTCAGTTA | CTCGGGAGGC | TGAGACAGGA | GAATTGCTTG | 120
| AACTCAAGAG | GCAGAGGTTG | CAGTGAGCCA | AGATTGAGCC | ACTACACCCC | AGCCTGGGTA | 180
| ACACAGGGAG | ACTCCATCTC | AAAAATAAAA | TAAAATAAAA | TAAACAGGAG | GAAGGAGCAG | 240
| CACCAAATCC | AAGATGGCGG | CCAGCAGGAG | GCTGATGAAG | GAGCTTGAAG | AAATCCGCAA | 300
| ATGTGGGATG | AAAAACTTCT | GTAACATCCA | GGTTGATGAA | GCTAATTTAT | TGACTTGGCA | 360
| AGGGCTTATT | GTTCCTGACA | ACCCTCCATA | TGATAAGGGG | GCCTTCAGAA | TAGAAATCAA | 420
| CTTTCCAGCA | GAGTACCCAT | TCAAACCACC | GAAGATCACA | TTTAAAACAA | AGATCTATCA | 480
| CCCAAACATC | GACGAAAAGG | GGCAGGTCTG | TCTGCCAGTA | ATTAGTGCTG | AAAACTGGAA | 540
| GCCAGCAACC | AAAACCGACC | AAGTAATCCA | GTCCCTCATA | GCACTGGTGA | ATGACCCCCA | 600
| GCCCAAGCAC | CCGCTTCGGG | CTGACCTAGC | TGAAGAATAC | TCTAAGGACC | GTAAAAAATT | 660
| CTGTAAGAAT | GCTGAAGAGT | TTACAAAGAA | ATATGGGAA | AAGCGACCTG | TGGACTAAAA | 720
| TCTGCCACGA | TTGGTTCCAG | CAAGTGTGAG | CAGAGACCCC | GTGCAGTGCA | TTCAGACACC | 780
| CCGCAAAGCA | GGACTCTGTG | GAAATTGACA | CGTGCCACCG | CCTGGCGTTC | GCTTGTGGCA | 840
| GTTACTAACT | TTCTACAGTT | TTCTTAATCA | AAAGTGGTCT | AGGTAACCTG | TAAAGAAAGG | 900
| ATTAAAAATT | TAAGATGTTC | TAGTTCTGCT | CTCTTTGTTT | TAAAAATCAC | TGCTTCAATC | 960
| TACTTCAAAA | GAAAAAAAAA | ACAATAAAAA | GTGTTGATGA | | | 1000

(2) INFORMATION FOR SEQ ID NO: 2:

(i) SEQUENCE CHARACTERISTICS:
        (A) LENGTH: 154 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION:1..154

(xi) SEQUENCE DESCRIPTION: SEQ ID NO: 2:

Met Ala Ala Ser Arg Arg Leu Met Lys Glu Leu Glu Glu Ile Arg Lys
1               5                   10                  15

Cys Gly Met Lys Asn Phe Cys Asn Ile Gln Val Asp Glu Ala Asn Leu
                20                  25                  30

Leu Thr Trp Gln Gly Leu Ile Val Pro Asp Asn Pro Pro Tyr Asp Lys
            35                  40                  45

Gly Ala Phe Arg Ile Glu Ile Asn Phe Pro Ala Glu Tyr Pro Phe Lys
        50                  55                  60

Pro Pro Lys Ile Thr Phe Lys Thr Lys Ile Tyr His Pro Asn Ile Asp
65                  70                  75                  80

Glu Lys Gly Gln Val Cys Leu Pro Val Ile Ser Ala Glu Asn Trp Lys
                85                  90                  95

Pro Ala Thr Lys Thr Asp Gln Val Ile Gln Ser Leu Ile Ala Leu Val

|     |     |     |     | 100 |     |     |     | 105 |     |     |     | 110 |     |
| --- | --- | --- | --- | --- | --- | --- | --- | --- | --- | --- | --- | --- | --- |
| Asn | Asp | Pro | Gln | Pro | Lys | His | Pro | Leu | Arg | Ala | Asp | Leu | Ala | Glu | Glu |
|     |     |     |     | 115 |     |     |     | 120 |     |     |     | 125 |     |

Tyr Ser Lys Asp Arg Lys Lys Phe Cys Lys Asn Ala Glu Glu Phe Thr
130                     135                 140

Lys Lys Tyr Gly Glu Lys Arg Pro Val Asp
145             150

(2) INFORMATION FOR SEQ ID NO: 3:

(i) SEQUENCE CHARACTERISTICS:
        (A) LENGTH: 683 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

```
AGCACCAAAT CCAAGATGGC GGCCAGCAGG AGGCTGATGA AGGAGCTTGA AGAAATCCGC    60
AAATGTGGGA TGAAAAACTT CCGTAACATC CAGGTTGATG AAGCTAATTT ATTGACTTGG   120
CAAGGGCTTA TTGTTCCTGA CAACCCTCCA TATGATAAGG GAGCCTTCAG AATCGAAATC   180
AACTTTCCAG CAGAGTACCC ATTCAAACCA CCGAAGATCA CATTTAAAAC AAAGATCTAT   240
CACCCAAACA TCGACGAAAA GGGGCAGGTC TGTCTGCCAG TAATTAGTGC CGAAAACTGG   300
AAGCCAGCAA CCAAAACCGA CCAAGTAATC CAGTCCCTCA TAGCACTGGT GAATGACCCC   360
CAGCCTGAGC ACCCGCTTCG GGCTGACCTA GCTGAAGAAT ACTCTAAGGA CCGTAAAAAA   420
TTCTGTAAGA ATGCTGAAGA GTTTACAAAG AAATATGGGG AAAAGCGACC TGTGGACTAA   480
AATCTGCCAC GATTGGTTCC AGCAAGTGTG AGCAGAGACC CCGTGCAGTG CATTCAGACA   540
CCCCGCAAAG CAGGACTCTG TGGAAATTGA CACGTGCCAC CGCCTGGCGT TCGCTTGTGG   600
CAGTTACTAA CTTTCTACAG TTTTCTTAAT CAAAAGTGGT CTAGGTAACC TGTAAAGAAA   660
GGATTAAAAA TTTAAGATGT TCT                                          683
```

(2) INFORMATION FOR SEQ ID NO: 4:

(i) SEQUENCE CHARACTERISTICS:
        (A) LENGTH: 659 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 4:

```
CAGAATTTGG ATAAATAGGA GGCAGATTTG GCTTAAAAGC ACATTAGCTG TAAATCAGTT    60
GTAAAGCCAG AGTTTTGTTC CCGGATTAGC TGCCTCTTGC CTGTGCCATT TCTGAGACTG   120
TGTTAACCCC CCATGAATTG TCCTTCTCTT GGCAGTAATC CAGTCCCTCA TAGCACTGGT   180
GAATGACCCC CAGCCTGAGC ACCCGCTTCG GGCTGACCTA GCTGAAGAAT ACTCTAAGGA   240
CCGTAAAAAA TTCTGTAAGA ATGCTGAAGA GTTTACAAAG AAATATGGGG AAAAGCGACC   300
TGTGGACTAA AATCTGCCAC GATTGGTTCC AGCAAGTGTG AGCAGAGACC CCGTGCAGTG   360
CATTCAGACA CCCCGCAAAG CAGGACTCTG TGGAAATTGA CACGTGCCAC CGCCTGGCGT   420
TCGCTTGTGG CAGTTACTAA CTTTCTACAG TTTTCTTAAT CAAAAGTGGT CTAGGTAACC   480
TGTAAAGAAA GGATTAAAAA TTTAAGATGT TCTAGTTCTG CTCTCTTTGT TTTAAAAATG   540
ACTGCTTCAA TCTACTTCAA AAGAATGGTG TTTCTTTTCT TGTCCAATTT TATCCAAAAT   600
```

```
CTTCAAGTTA CATTTAACCC ATAAGGTTTA AAAAAAAGGA AAAAAAACGG TTGTGGTTC        659
```

(2) INFORMATION FOR SEQ ID NO: 5:

(i) SEQUENCE CHARACTERISTICS:
        (A) LENGTH: 154 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

```
Met Ala Ala Ser Arg Arg Leu Met Lys Glu Leu Glu Glu Ile Arg Lys
 1               5                  10                  15

Cys Gly Met Lys Asn Phe Arg Asn Ile Gln Val Asp Glu Ala Asn Leu
                20                  25                  30

Leu Thr Trp Gln Gly Leu Ile Val Pro Asp Asn Pro Pro Tyr Asp Lys
         35                  40                  45

Gly Ala Phe Arg Ile Glu Ile Asn Phe Pro Ala Glu Tyr Pro Phe Lys
 50                  55                  60

Pro Pro Lys Ile Thr Phe Lys Thr Lys Ile Tyr His Pro Asn Ile Asp
65                  70                  75                  80

Glu Lys Gly Gln Val Cys Leu Pro Val Ile Ser Ala Glu Asn Trp Lys
                85                  90                  95

Pro Ala Thr Lys Thr Asp Gln Val Ile Gln Ser Leu Ile Ala Leu Val
                100                 105                 110

Asn Asp Pro Gln Pro Glu His Pro Leu Arg Ala Asp Leu Ala Glu Glu
            115                 120                 125

Tyr Ser Lys Asp Arg Lys Lys Phe Cys Lys Asn Ala Glu Glu Phe Thr
    130                 135                 140

Lys Lys Tyr Gly Glu Lys Arg Pro Val Asp
145                 150
```

(2) INFORMATION FOR SEQ ID NO: 6:

(i) SEQUENCE CHARACTERISTICS:
        (A) LENGTH: 464 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 6:

```
GAAGAAATAT GCAATTGTGG AATGAAAAAC TTCCGTAACT TCCAGGTAGA TGGAGCTAAT         60

TTATTGACTT GGCAAGGGCT TATTGTTCCT GACAACCCTC CATATAAGGG GGCCTTCAGA        120

ATCGAAATCA ACTTTCCAGC AGAGCACCCA TTCAAACCAC CGAAGAGCAC ACTTAAAGAT        180

CTGTCACCCA AATGTCCACT AAAAGGGGCA GGTCTCTCTG CCAGTAAATT AGTGCTGAAA        240

ACTGGAAGCC AGCAACCAAA ACTGACCAAG TAATCCAGTC CCTCACAGCA CTGGTGAATG        300

ACCCCCAGCC TGAGCATCCA CTTCAGGCTG ACCTAGCTGA ATAATACTCT AAGGACTGTA        360

AATATTTCTG TAAGAATGCT GAAGTTTACA GAGAAATAGG GGGAAAAGCG ACTTGTAGAC        420

TAAAATCTGC CACAATTGGC TCCAGTAAGT GTGAGCAGAG ACCC                         464
```

(2) INFORMATION FOR SEQ ID NO: 7:

(i) SEQUENCE CHARACTERISTICS:
        (A) LENGTH: 90 amino acids (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION:1..154

(xi) SEQUENCE DESCRIPTION: SEQ ID NO: 7:

Glu Glu Ile Cys Asn Cys Gly Met Lys Asn Phe Arg Asn Phe Gln Val
1               5                   10                  15

Asp Gly Ala Asn Leu Leu Thr Trp Gln Gly Leu Ile Val Pro Asp Asn
            20                  25                  30

Pro Pro Tyr Lys Gly Ala Phe Arg Ile Glu Ile Asn Phe Pro Ala Glu
        35                  40                  45

His Pro Phe Lys Pro Pro Lys Ser Thr Leu Lys Asp Leu Ser Pro Lys
    50                  55                  60

Cys Pro Leu Lys Gly Ala Gly Leu Ser Ala Ser Lys Leu Val Leu Lys
65                  70                  75                  80

Thr Gly Ser Gln Gln Pro Lys Leu Thr Lys
                85                  90

(2) INFORMATION FOR SEQ ID NO: 8:

(i) SEQUENCE CHARACTERISTICS:
        (A) LENGTH: 361 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 8:

AACTGGAAGC CAGCCACCAA GACTGTCCAA GTAATCCAGT CCCTCATAGC ACTGGTGAAT      60

GACCCCCAGC CTGAGCACCC ACTCCGGGCT GACCTAGCTG AAGAATACTC TAAGGACCGT     120

AAAAAATTCT GTAAGAATGC TGAAGAGTTT ACAAAGAAAT ATGGGGAAAA GCGACCTGTG     180

GACTAAAATC TGCCACGATT GGTTCCAGCA AGTGTGAGCA GAGACCCCGA GCAGTGCATT     240

CAGACACCCC GCAAAGCAGG ACTCTGTGGA AATTGACACG TGCCACCAAC TGGCGTCCGC     300

TTGTGGCAGT TACTAACTTT CTACAGTTTT CTTAATCAAA AGTGGTCTAG GTAACCTGTA     360

A                                                                    361

(2) INFORMATION FOR SEQ ID NO: 9:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

Asn Trp Lys Pro Ala Thr Lys Thr Val Gln Val Ile Gln Ser Leu Ile
1               5                   10                  15

Ala Leu Val Asn Asp Pro Gln Pro Glu His Pro Leu Arg Ala Asp Leu
            20                  25                  30

Ala Glu Glu Tyr Ser Lys Asp Arg Lys Lys Phe Cys Lys Asn Ala Glu
        35                  40                  45

Glu Phe Thr Lys Lys Tyr Gly Glu Lys Arg Pro Val Asp

```
            50              55           60
```

(2) INFORMATION FOR SEQ ID NO: 10:

(i) SEQUENCE CHARACTERISTICS:
        (A) LENGTH: 18 nucleotides
        (B) TYPE: nucleic acids
        (C) STRANDEDNESS: single
        (D) TOPOLOGY: linear (ii) MOLECULE TYPE: DNA (xi) SEQUENCE DESCRIPTION: SEQ ID NO: 10:

```
GGCAGGTCTG TCTGCCAG                                          18
```

(2) INFORMATION FOR SEQ ID NO: 11:

(i) SEQUENCE CHARACTERISTICS:
        (A) LENGTH: 21 nucleotides
        (B) TYPE: nucleic acids
        (C) STRANDEDNESS: single
        (D) TOPOLOGY: linear (ii) MOLECULE TYPE: DNA (xi) SEQUENCE DESCRIPTION: SEQ ID NO: 11:

```
GGTCTCTGCT CACACTTGCT G                                      21
```

(2) INFORMATION FOR SEQ ID NO: 12:

(i) SEQUENCE CHARACTERISTICS:
        (A) LENGTH: 21 nucleotides
        (B) TYPE: nucleic acids
        (C) STRANDEDNESS: single
        (D) TOPOLOGY: linear (ii) MOLECULE TYPE: DNA (xi) SEQUENCE DESCRIPTION: SEQ ID NO: 12:

```
CAGCAAGTGT GAGCAGAGAC C                                      21
```

(2) INFORMATION FOR SEQ ID NO: 13:

(i) SEQUENCE CHARACTERISTICS:
        (A) LENGTH: 22 nucleotides
        (B) TYPE: nucleic acids
        (C) STRANDEDNESS: single
        (D) TOPOLOGY: linear (ii) MOLECULE TYPE: DNA (xi) SEQUENCE DESCRIPTION: SEQ ID NO: 13:

```
CTTTACAGGT TACCTAGACC AC                                     22
```

(2) INFORMATION FOR SEQ ID NO: 14:

(i) SEQUENCE CHARACTERISTICS:
        (A) LENGTH: 21 nucleotides
        (B) TYPE: nucleic acids
        (C) STRANDEDNESS: single
        (D) TOPOLOGY: linear (ii) MOLECULE TYPE: DNA (xi) SEQUENCE DESCRIPTION: SEQ ID NO: 14:

```
GAAGCCAGCA ACCAAAACCG A                                      21
```

(2) INFORMATION FOR SEQ ID NO: 15:

(i) SEQUENCE CHARACTERISTICS:
    (A) LENGTH: 18 nucleotides
    (B) TYPE: nucleic acids
    (C) STRANDEDNESS: single
    (D) TOPOLOGY: linear (ii) MOLECULE TYPE: DNA (xi) SEQUENCE DESCRIPTION: SEQ ID NO: 15:

CACAAGCGAA CGCCAGGC                                        18

(2) INFORMATION FOR SEQ ID NO: 16:

(i) SEQUENCE CHARACTERISTICS:
        (A) LENGTH: 19 nucleotides
        (B) TYPE: nucleic acids
        (C) STRANDEDNESS: single
        (D) TOPOLOGY: linear (ii) MOLECULE TYPE: DNA (xi) SEQUENCE DESCRIPTION: SEQ ID NO: 16:

CCAGCCTGAG CACCCGCTT                                       19

(2) INFORMATION FOR SEQ ID NO: 17:

(i) SEQUENCE CHARACTERISTICS:
        (A) LENGTH: 19 nucleotides
        (B) TYPE: nucleic acids
        (C) STRANDEDNESS: single
        (D) TOPOLOGY: linear (ii) MOLECULE TYPE: DNA (xi) SEQUENCE DESCRIPTION: SEQ ID NO: 17:

TAGGAGGCAG CTTTGGCTT                                       19

(2) INFORMATION FOR SEQ ID NO: 18:

(i) SEQUENCE CHARACTERISTICS:
        (A) LENGTH: 18 nucleotides
        (B) TYPE: nucleic acids
        (C) STRANDEDNESS: single
        (D) TOPOLOGY: linear (ii) MOLECULE TYPE: DNA (xi) SEQUENCE DESCRIPTION: SEQ ID NO: 18:

CCAGCCTCGC CAATATGG                                        18

(2) INFORMATION FOR SEQ ID NO: 19:

(i) SEQUENCE CHARACTERISTICS:
        (A) LENGTH: 19 nucleotides
        (B) TYPE: nucleic acids
        (C) STRANDEDNESS: single
        (D) TOPOLOGY: linear (ii) MOLECULE TYPE: DNA (xi) SEQUENCE DESCRIPTION: SEQ ID NO: 19:

GGTGTCTGAA TGCACTGCA                                       19

(2) INFORMATION FOR SEQ ID NO: 20:

(i) SEQUENCE CHARACTERISTICS:
        (A) LENGTH: 21 nucleotides
        (B) TYPE: nucleic acids
        (C) STRANDEDNESS: single
        (D) TOPOLOGY: linear

```
    (ii) MOLECULE TYPE: DNA (xi) SEQUENCE DESCRIPTION: SEQ ID NO: 20:

GCGGCCAGCA GGAGGCTGAT G                                              21

(2) INFORMATION FOR SEQ ID NO: 21:

(i) SEQUENCE CHARACTERISTICS:
        (A) LENGTH: 18 nucleotides
        (B) TYPE: nucleic acids
        (C) STRANDEDNESS: single
        (D) TOPOLOGY: linear (ii) MOLECULE TYPE: DNA (xi) SEQUENCE DESCRIPTION: SEQ ID NO: 21:

GTCTGAATGC ACTGCACG                                                  18
```